United States Patent
Kohr

(10) Patent No.: US 8,021,870 B2
(45) Date of Patent: *Sep. 20, 2011

(54) METHOD OF BIOTREATING A SOLID MATERIAL COMPRISING AN ORGANIC COMPOUND

(75) Inventor: William J. Kohr, San Mateo, CA (US)

(73) Assignee: Geobiotics, LLC, Lakewood, CO (US)

( * ) Notice: Subject to any disclaimer, the term of this patent is extended or adjusted under 35 U.S.C. 154(b) by 191 days.

This patent is subject to a terminal disclaimer.

(21) Appl. No.: 12/198,885

(22) Filed: Aug. 26, 2008

(65) Prior Publication Data

US 2008/0311647 A1    Dec. 18, 2008

Related U.S. Application Data

(63) Continuation of application No. 10/971,331, filed on Oct. 21, 2004, now Pat. No. 7,416,882, which is a continuation of application No. 10/176,854, filed on Jun. 20, 2002, now Pat. No. 6,855,527, which is a continuation of application No. 09/735,156, filed on Dec. 12, 2000, now Pat. No. 6,410,304, which is a continuation of application No. 09/097,316, filed on Jun. 12, 1998, now Pat. No. 6,159,726, which is a continuation of application No. 08/636,117, filed on Apr. 22, 1996, now Pat. No. 5,766,930, which is a continuation-in-part of application No. 08/588,589, filed on Jan. 18, 1996, now Pat. No. 6,083,730, which is a continuation-in-part of application No. 08/459,621, filed on Jun. 2, 1995, now abandoned.

(51) Int. Cl.
    C12P 3/00    (2006.01)
    C02F 3/34    (2006.01)
    B09C 1/10    (2006.01)

(52) U.S. Cl. ............ 435/262; 435/168; 435/262.5; 435/264; 435/281; 435/282

(58) Field of Classification Search .................. None
See application file for complete search history.

(56) References Cited

U.S. PATENT DOCUMENTS

| | | | |
|---|---|---|---|
| 588,476 A | 8/1897 | Rhodes |
| 3,647,261 A | 3/1972 | Stenger et al. |
| 3,777,004 A | 12/1973 | Lankenau et al. |
| 3,796,308 A | 3/1974 | McIlhinney et al. |
| 3,819,797 A | 6/1974 | Spedden et al. |
| 3,949,051 A | 4/1976 | Pawlek |
| 4,017,309 A | 4/1977 | Johnson |
| 4,056,261 A | 11/1977 | Darrah |
| 4,173,519 A | 11/1979 | Parker et al. |
| 4,256,705 A | 3/1981 | Heinen et al. |
| 4,256,706 A | 3/1981 | Heinen et al. |
| 4,269,699 A | 5/1981 | McCready et al. |
| 4,279,868 A | 7/1981 | Von Kohorn |
| 4,301,121 A | 11/1981 | Von Kohorn |
| 4,318,892 A | 3/1982 | Von Kohorn |
| 4,324,764 A | 4/1982 | Hasegawa et al. |
| 4,343,773 A | 8/1982 | Miller et al. |
| 4,374,097 A | 2/1983 | Holland |
| 4,402,831 A | 9/1983 | Beardsmore et al. |
| 4,424,194 A | 1/1984 | Hughes |
| 4,526,615 A | 7/1985 | Johnson |
| 4,557,905 A | 12/1985 | Sherman et al. |
| 4,571,387 A | 2/1986 | Bruynesteyn et al. |
| 4,585,548 A | 4/1986 | Cadzow et al. |
| 4,690,894 A | 9/1987 | Brierley et al. |
| 4,721,526 A | 1/1988 | Elmore et al. |
| 4,729,788 A | 3/1988 | Hutchins et al. |
| 4,740,243 A | 4/1988 | Krebs-Yuill et al. |
| 4,752,332 A | 6/1988 | Wu et al. |
| 4,778,519 A | 10/1988 | Pesic |
| 4,789,481 A | 12/1988 | Brierley et al. |
| 4,888,293 A | 12/1989 | Hackl et al. |
| 4,987,081 A | 1/1991 | Hackl et al. |
| 5,006,320 A | 4/1991 | Reid et al. |
| 5,007,620 A | 4/1991 | Emmett, Jr. et al. |
| H1074 H | 7/1992 | Lazaroff et al. |
| 5,127,942 A | 7/1992 | Brierley et al. |
| 5,196,052 A | 3/1993 | Gross et al. |
| 5,232,676 A | 8/1993 | Wolff et al. |

(Continued)

FOREIGN PATENT DOCUMENTS

AU    749366    2/1999

(Continued)

OTHER PUBLICATIONS

F. Acevedo et al., "Comparative performance of stirred and pachuca tanks in the bioleaching of a copper concentrate", Biohydrometallurgy, pp. 385-394 (Warwick United Kingdom: Science and Technology Letters) (1987).

(Continued)

Primary Examiner — Herbert J Lilling
(74) Attorney, Agent, or Firm — Dickstein Shapiro LLP

(57) ABSTRACT

A method of biotreating a solid material including an organic compound is provided. According to the method, a nonstirred bioreactor having a void volume of greater than or equal to 25% with a mixture including a solid material to be biotreated and a plurality of coarse substrates having a particle size greater than or equal to about 0.6 cm is formed. The solid material to be biotreated includes an organic material. The mixture includes sufficient coarse substrates to provide the reactor with at least 100 square meters of surface area per cubic meter of reactor space. The solid material in the bioreactor is biotreated until the organic material within the bioreactor is reduced to a desired concentration.

8 Claims, 9 Drawing Sheets

U.S. PATENT DOCUMENTS

| | | | |
|---|---|---|---|
| 5,236,677 A | 8/1993 | Torres-Cardona et al. | |
| 5,244,493 A | 9/1993 | Brierley et al. | |
| 5,246,486 A | 9/1993 | Brierley et al. | |
| 5,332,559 A | 7/1994 | Brierley et al. | |
| 5,356,457 A | 10/1994 | Pincheira Alvarez et al. | |
| 5,431,717 A | 7/1995 | Kohr | |
| 5,462,720 A | 10/1995 | Aragones | |
| 5,527,382 A | 6/1996 | Pincheira Alvarez et al. | |
| 5,573,575 A | 11/1996 | Kohr | |
| 5,611,839 A | 3/1997 | Kohr | |
| 5,676,733 A | 10/1997 | Kohr | |
| 5,763,259 A | 6/1998 | Paños | |
| 5,766,930 A | 6/1998 | Kohr | |
| 5,800,593 A | 9/1998 | Kohr | |
| 5,834,294 A | 11/1998 | Brierley et al. | |
| 5,873,927 A | 2/1999 | Schaffner et al. | |
| 5,914,441 A | 6/1999 | Hunter et al. | |
| 6,083,730 A | 7/2000 | Kohr | |
| 6,096,113 A | 8/2000 | Schaffner et al. | |
| 6,107,065 A | 8/2000 | Kohr | |
| 6,159,726 A | 12/2000 | Kohr | |
| 6,383,458 B1 | 5/2002 | Brierley et al. | |
| 6,410,304 B2 | 6/2002 | Kohr | |
| 6,696,283 B1 | 2/2004 | Brierley et al. | |
| 6,855,527 B2 | 2/2005 | Kohr | |
| 7,416,882 B2 | 8/2008 | Kohr | |

FOREIGN PATENT DOCUMENTS

| | | |
|---|---|---|
| EP | 0 522 978 A1 | 1/1993 |
| EP | 0 646 642 A2 | 4/1995 |
| GB | 2180829 A | 4/1987 |
| HU | 204 900 B | 1/1991 |
| WO | WO 95/15403 | 6/1995 |

OTHER PUBLICATIONS

L. Ahonen et al., "Redox Potential-Controlled Bacterial Leaching of Chalcopyrite Ores", Biohydrometallurgical Technologies, The Minerals, Metals & Materials Society (1993) pp. 571-578.

L. Ahonen and O. H. Tuovinen, "Bacterial leaching of complex sulfide ore samples in bench-scale column reactors", Hydrometallurgy 37, pp. 1-21 (1995).

G.F. Andrews et al., "Combined physical/microbial beneficiation of coal using the flood/drain bioreactor", Fuel Processing Technology 40, pp. 2-33, 283-296 (1994).

Piero M. Armenante, "Bioreactors", Biotreatment of Industrial and Hazardous Waste, M. A. Levin and M. A. Gealt, Chap. 4, pp. 65-112 (McGraw-Hill, New York) (1993).

Y. A. Attia et al., "Cleaning and desulfurization of high-sulfur coal by selective flocculation and bioleaching in a draft tube fluidized bed reactor", Processing and Utilization of High-Sulfur Coals IV (Elsevier Science Publishers B.V., Amsterdam) (1991).

A. D. Bailey and G. S. Hansford, "Effect of removal of unattached cells on the bio-oxidation rate of pyrite in a fluidised bed reactor", Biotech. Lett., vol. 15, No. 5, pp. 543-548 (1993).

A. D. Bailey and G. S. Hansford, "A fluidised bed reactor as a tool for the investigation of oxygen availability on the biooxidation rate of sulphide minerals at high solids concentrations", Minerals Eng., vol. 6, No. 4, pp. 387-396 (1993).

V. Bakoyianis and A.A. Koutinas, "A Catalytic Multistage Fixed-Bed Tower Bioreactor in an INdustrial-Scale Pilot Plant for Alcohol Production", Biotechnology and Bioengineering, Vol. 49, pp. 197-203 (1996).

J. W. Bennett et al., "Limitations on pyrite oxidation rates in dumps set by air transport mechanisms", International Symposium of Biohydrometallurgy, pp. 551-561 (Warwick, United Kingdom: Science and Technology Letters) (1987).

M. Beyer, "Microbial removal of pyrite from coal using a percolation bioreactor", Biotech. Letters, vol. 9, No. 1, pp. 19-24 (1987).

M. L. Blasquez et al., "Coal biodesulphurization: A review", Biorecovery, vol. 2, pp. 155-177 (1993).

M. Boon et al., "Mechanisms and Rate Limiting Steps in Bioleaching of Sphalerite, Chalcopyrite and Pyrite with *Thiobacillus ferrooxidans*," Biohydrometallurgical Technologies, pp. 217-235 (Jackson Hole, Wyoming: The Minerals, Metals and Materials Society (1993).

C. L. Brierley, "Mineral Bio-Processing: Opportunities in Extractive Metallurgy and Environmental Control", NIST, Nov. 1993, pp. 1-29.

J. A. Brierley et al., "Biooxidation-Heap Concept for Pretreatment of Refractory Gold Ore", Biohydrometallurgical Technologies, pp. 1-30, (Jackson Hole, Wyoming: The Minerals, Metals and Materials Society (1993).

J. A. Brierley, "Bacterial Processes for Transformation of Metals", Environmental Speciation and Monitoring Needs for Trace Metal-Containing Substances from Energy-Related Processes, pp. 264-273 (Proceedings of the DOE/NBS Workshop held at National Bureau of Standards, Gaithersburg, Maryland, May 18-20, 1981).

R. E. Browner et al., "Studies on the Heap Leaching Characteristics of Western Australian Gold Ores", World Gold (1991).

Al Bruynesteyn, "Biological Treatment of Refractory Gold Ores—Advantages and Disadvantages", BioMine '93, 3-1 to 3-7 (Adelaide, South Australia, Australian Mineral Foundation) (1993).

Julia R. Budden et al., "Pilot Plant Test Work and Engineering Design for the BacTech Bacterial Oxidation Plant at the Youanmi Mine", BioMine '94, 4.1 to 4.8 (Perth, South Australia, Australian Mineral Foundation) (Sep. 19-20, 1994).

Julia R. Budden, "Bacterial Oxidation Fact and Fallacy", BioMine '93, 19-1 to 19-3 (Adelaide, South Australia, Australian Mineral Foundation) (1993).

A. Burbank et al., "Biooxidation of Refractory Gold Ores in Heaps", Advances in Gold and Silver Processing at GOLDTech 4 (Society of Mining, Metallurgy and Exploration, Inc.) (1990).

Paul D. Chamberlin, "Status of Heap, Dump, and in Situ Leaching of Gold and Silver", World Gold, pp. 225-232 (1989).

Marie-Noelle Collinet et al., "Characterization of arsenopyrite oxidizing *Thiobacillus*. Tolerance of arsenite, arsenate, ferrous and ferric iron", vol. 57, pp. 237-244, (Antonie van Leeuwenhoek) (1990).

M. A. Cornachione et al., "Laboratory Investigation of Bio-Heap Leaching to Remove Sulfer from Kiln Feed Materials", Mining Engineering, pp. 153-156 (Feb. 1994).

M. T. Corral et al., "Continuous Bioleaching of Mineral Sulphide", Biohydrometallurgical Technologies (Jackson Hole, Wyoming: The Minerals, Metals and Materials Society (1993).

K. Czeschka et al., "Influence of biosurfactant producing microorganisms on the hydrocarbon degradation by an original soil population in a percolated soil fixed bed reactor," (Institut für Biochemie und Biotechnolgie, Germany), Jour-Soil Decontam Using Bio Processes (Dec. 1992).

Laura L. Damon, "Heap Leach Study of Gilt Edge Sulfide Ore", Black Hills Fifth Western Reg. Conf. on Precious Metals, Coal and the Environment, pp. 47-59 (1994).

J. C. Duarte et al., "Semi-Conductor Reactor Studies of a High Temperature Copper Bioleaching Process", Proceedings of the 6th European Congress on Biotechnology (1994), pp. 1177-1180.

H. L. Ehrlich, "Bioleaching of silver from a mixed sulfide ore in a stirred reactor", Biohydrometallurgy, pp. 223-231 (Warwick, United Kingdom: Science and Technology Letters) (1987).

Fraser, K.S., et al., Processing of Refractory Gold Ores, Minerals Engineering, vol. 4, Nos. 7-11, pp. 1029-1041, 1991.

G. M. Fraser, "Mixing and Oxygen Transfer in Mineral Bioleaching", pp. 16.1-16.11, (Biomine '93 Conference, Mar. 22-23, 1993, Adelaide, South Africa).

"Slurry Biodegradation", Hazardous Waste Remediation: Innovative Treatment Technologies, Chap. 4, pp. 29-35 (Edited by H. M. Freeman and E. F. Harris. Technomic Publishing Co., Inc. (1995).

"Composting of Contaminated Soil", Hazardous Waste Remediation: Innovative Treatment Technologies, Chap. 8, pp. 73-86 (Edited by H. M. Freeman and E. F. Harris. Technomic Publishing Co., Inc. (1995).

"Heap Pile Bioremediation", Hazardous Waste Remediation: Innovative Treatment Technologies, Chap. 9, pp. 87-100 (Edited by H. M. Freeman and E. F. Harris. Technomic Publishing Co., Inc. (1995).

Chunsheng Fu et al., "Studies on Contaminant Biodegradation in Slurry, Wafer, and Compacted Soil Tube Reactors," Environ. Sci. Technol., vol. 30, No. 3. pp. 743-750 (1996).

Marcel J. Geerdink et al., "Model for microbial degradation of nonpolar organic contaminants in a soil slurry reactor," Environ. Sci. Technol., vol. 30, pp. 779-796. (1996).

Murray R. Gray et al., "Biological remediation of anthracene-contaminated soil in rotating bioreactors." Appl. Microbiol. Biotechnol., vol. 40, pp. 933-940 (1994).

E. A. Griffin et al., "Bioreactor development with respect to process constraints imposed by bio-oxidation and waste remediation," Appl. Biochem. and Biotech, vols. 24-25, pp. 627-635 (1990).

Ralph P. Hackl, "Operating a commercial-scale bioleach reactor at the Congress gold property," Mining Engineering, vol. 42(12), pp. 1325-1326 (1990).

G. S. Hanford et al., "A propagating-pore model for the batch bioleach kinetics of refractory gold-bearing pyrite", pp. 345-358 (Warwick, United Kingdom: Science and Technology Letters) (1987).

J. R. Harries et al., "Rate controls on leaching in pyritic mine wastes", BioHydroMetallurgy (1987) (Warwick, United Kingdom), Science and Technology Letters, pp. 233-241.

J. G. Harrington et al., "Engineering Aspects of Heap Biooxidation of Course-Crushed Refractory Gold Ores", Biohydrometallurgical Technologies, The Minerals, Metals & Materials Society (1993) pp. 521-530.

J. G. Harrington et al., "Kinetics of Biooxidation of Coarse Refractory Gold Ores", Hydrometallurgy: Fundamentals, Technologies and Innovations (Society of Mining, Metallurgy and Exploration) (Salt Lake City 1993).

K. L. Henley et al., "The Mineralogy of Refractory Gold Ores", Biomine '93 Conference, Mar. 22-23, 1993, Adelaide, Australia, pp. 5.1-5.13.

M. N. Herrera et al., "A Phenomenological Model of the Bioleaching of Complex Sulfide Ores", Hydrometallurgy, vol. 22, pp. 193-206 (1989).

Warwick Hoffmann et al., "Design of a reactor bioleach process for refractory gold treatment," FEMS Micro. Rev., vol. 11(1-3), pp. 221-230 (1993).

B. C. Kelley et al., "Bioremediation—Applications to Waste Processing in the Mining Industry" Biomine '93 Conference, Mar. 22-23, 1993, Adelaide, Australia, pp. 10.1-10.10.

R. W. Lawrence, "Biotreatment of Gold Ores", Microbial Mineral Recovery, pp. 127-148 (H.L. Ehrlich and C.L. Brierley, Editors—1990, McGraw-Hill, New York).

Eric Livesey-Goldblatt, "Bacterial Leaching of Gold, Uranium, Pyrite Bearing Compacted Mine Tailing Slimes", Fundamental and Applied Biohydrometallurgy, Proceedings of the Sixth International Symposium on Biohydrometallurgy, pp. 89-96 (Vancouver, B.C., Canada) (1985).

Andrew G. Livingston, "Biodegradation of 3,4-dichloroaniline in a fluidized bed bioreactor and a steady-state biofilm kinetic model," Biotech. and Bioeng., vol. 38, pp. 260-272 (1991).

H. M. Lizama et al., "Bacterial Leaching of Copper and Zinc From a Sulfide Ore by a Mixed Culture of *Thiobacillus* Ferrooxidants and *Thiobacillus* Thiooxidants in Laboratory Scale and Pilot Plant Scale Columns", Biohydrometallurgy (1989) pp. 519-531.

G. Loi et al., "Bioreactor performance versus solids concentration in coal biodepyritization," Fuel Processing Technology, vol. 40, pp. 251-260 (1994).

Jock McGregor and Gene E. McClelland, "Agglomeration with Pulp: A Concept to Improve the Economics of Heap leaching", Randol Gold Forum, pp. 150-152 (Sacramento, CA, 1989).

J. Merson, "Mining With Microbes", New Scientist, Jan. 4, 1991, pp. 17-19.

B. Mihaylov et al., "Biooxidation of a Sulfide Gold Ore in Columns", Mineral Bioprocessing, The Minerals, Metals & Materials Society (1993) pp. 163-177.

B. Mihaylov et al., "Gold Recovery from a Low-Grade Ore Employing biological Pretreatment in Columns", Biohydrometallurgical Technologies, The Minerals, Metals & Materials Society (1993) pp. 499-511.

Miller et al., Bacterial Heap Leaching of Low-Grade Nickel Material, Council for Mineral Technology, Randburg, South Africa (1985), pp. 341-352.

D. Morin and P. Ollivier, "Pilot practice of continuous bioleaching of a refractory gold sulfide concentrate with a high As content", Biohydrometallurgy, pp. 563-576 (1989).

H. Nicholson et al., "Selection of a Refractory Gold Treatment Process for the Sansu Project", pp. 20-1 to 20.11, Ashanti Goldfields Corporation (Ghana) Limited, BioMine (Mar. 1993).

A. Nishiwaki et al., "Effect of longitudinal mixing on microbial growth in a multi-stage column reactor," J. Chem. Tech. Biotechnol., vol. 48, pp. 227-237 (1989).

Paul A.R. Odd et al., "Bioleaching—A Feasible Process for Wiluna Refractory Gold Ores", BioMIne'93, 1993 (Adelaide, South Australia), Australian Mineral Foundation.

P. Ollivier and D. Morin, "Bioleaching of Sulfide Concentrates and Ores: Study of Refractory Gold and Non-Ferrous Base Metals Ores", pp. 93-99, Randol Gold Forum (1990) (Olympic Valley, California), Randol International.

C. Ongcharit et al., "Novel Immobilized Cell Reactor for Microbial Oxidation of H2S", Chemical Engineering Science, vol. 45, No. 8, pp. 2383-2389 (1990).

G. Pantelis et al., "Optimising Oxidation Rates in Heaps in Pyritic Material", Biohydrometallurgical Technologies, The Minerals, Metals & Materials Society, pp. 731-738 (1993).

G. M. Potter, "Designs Factors for Heap Leaching Operations", Mining Engineering, pp. 277-281 (1981).

J. Parthen et al., "Determination of Technical Parameters for Microbial Soil Cleaning in Bioreactors", DECHEMA Biotechnology Conferences, vol. 4, Part A, pp. 563-567 (1990).

Tommy J. Phelps et al., "Biodegradation of Mixed-Organic Wastes by Microbial Consortia in Continuous-Recycle Expanded-Bed Bioreactors", Envir. Sci. Technol., vol. 25, No. 8, pp. 1461-1465 (1991).

A. Pinches et al., "The Performance of Bacterial Leach Reactors for the Pre-oxidation of Refractory Gold-Bearing Sulphide Concentrates", Biohydrometallurgy, pp. 329-344 (Warwick, United Kingdom, Antony Rowe Ltd.) (1987).

A. I.M. Ritchie et al., "Optimisation of Oxidation Rates in Dump Oxidation of Pyrite-Gold Ores", Bionnine '93 Conference, Mar. 22-23, 1993, Adelaide, Australia, pp. 9.1-9.8.

Hee W. Ryu et al., "Microbial coal desulfurization in an airlift bioreactor by sulfur-oxidizing bacterium *Thiobacillus ferrooxidans*", Fuel Processing Technology, vol. 36, pp. 267-275 (1993).

S. Sandhya et al., "Kinetics of Fe2+ Oxidation in Down Flow Packed Bed Fixed Film Reactors", J. Environ. Sci. Health, A27(2); pp. 445-461 (1992).

Silver et al., "Oxidation of metal sulfides by *Thiobacillus ferrooxidans* grown on different substrates", Can. J. Microbiol (1974), 20: pp. 141-147.

Southwood et al., Parameters Affecting the Bacterial Heap Leaching of Low-Grade Nicheliferous Material, Editions GEDIM, St. Etienne, France (1985), pp. 400-412.

T. V. Subrahmanyam et al., "Recovery Problems in Gold Ore Processing with Emphasis on Heap Leaching", Mineral Processing and Extractive Metallurgy Review, vol. 4, pp. 201-215 (1989).

A. Torma, "Mineral Bioprocessing", Biomine '93 Conference, Mar. 22-23, 1993, Adelaide, Australia, pp. 1.1-1.10.

Troy, M. A. et al., "Biological Land Treatment of Diesel Fuel-Contaminated Soil: Emergency Response Through Closure," Bioremediation: Field Experience, pp. 145-160 (Boca Raton, Lewis) (1994).

Tuovinen, O. et al., "Studies on the growth of *Thiobacillus ferrooxidans*", II. Toxicity of Uranimum to growing cultures and tolerance conferred by mutation, other metal cations and EDTA, Arch. Microbiol. (1974), pp. 153-164.

Untung, S.R., et al., Application of Bio-Leaching to Some Indonesian Sulphide Ores (A Preliminary Study), BioMine '93 Conference, Mar. 22-23, 1993, Adelaide, Australia, pp. 11.1-11.10.

Oren F. Webb et al., "Development of a Packed Bed Reactor System for Measurement of Xenobiotic Degradation by Microbial Cultures and of Soil Properties" (Abstract), 207th ACS National Meeting (American Chemical Society, San Diego, CA.) (1994).

Xin-Hui Xing et al., "A model analysis of microbial retainment process in porous support particles in a fluidized bed wastewater treatment reactor," J. Chem. Eng. Japan, vol. 25, No. 1, pp. 89-95 (1992).

Official Notification dated Jul. 30, 1999 from the Hungarian Patent Office for Hungarian National Phase Patent Application No. P9900904 (without translation) and attached Novelty Search Report dated May 19, 1999 from the Hungarian Patent Office for Hungarian National Patent Application No. P9900904 (and translation thereof).

K. Czeschka et al., "Heap Leach Study of Gilt Edge Sulfide Ore", Black Hills Fifth Western Reg. Conf. on Precious Metals, Coal and the Environment, pp. 47-59 (1994).

Anonymous, Study Shows Improved Gold Extraction, The Mining Record (1993).

METHOD OF BIOTREATING A SOLID MATERIAL COMPRISING AN ORGANIC COMPOUND

PRIORITY INFORMATION

This application is a continuation of U.S. patent application Ser. No. 10/971,331, filed Oct. 21, 2004, now U.S. Pat. No. 7,416,882, which is a continuation of U.S. patent application Ser. No. 10/176,854, filed Jun. 20, 2002, now U.S. Pat. No. 6,855,527, which is a continuation of U.S. patent application Ser. No. 09/735,156, filed Dec. 12, 2000, now U.S. Pat. No. 6,410,304, which is a continuation of Ser. No. 09/097,316, filed Jun. 12, 1998, now U.S. Pat. No. 6,159,726, which is a continuation of U.S. patent application Ser. No. 08/636,117, filed Apr. 22, 1996, now U.S. Pat. No. 5,766,930, which is a continuation-in-part of U.S. patent application Ser. No. 08/588,589, filed Jan. 18, 1996, now U.S. Pat. No. 6,083,730, which is a continuation-in-part of U.S. patent application Ser. No. 08/459,621, filed Jun. 2, 1995, now abandoned. Each of the foregoing applications is incorporated herein by reference as if fully set forth.

TECHNICAL FIELD

The present invention relates to the biotreatment of solid materials. In particular, the present invention relates to the ex situ biotreatment of solid materials in an aerobic process to degrade an undesired compound present in the solid material.

BACKGROUND ART

Biological treatment processes are finding application throughout industry. Such processes have been used in waste water treatment, hazardous waste remediation, desulfurization of coal, and biooxidation of refractory sulfide ores.

A variety of methods can be employed in the biological treatment of solid materials, including in situ treatment, landfarming, composting, heap treatment, and stirred or agitated tanks. In the ex situ biological treatment of solid materials, some sort of bioreactor is used to carry out the biotreatment. A bioreactor can be defined as a vessel or body in which biological reactions are carried out by microorganisms, or enzymes they produce, contained within the reactor itself. The main objective in the design of a bioreactor is to generate an optimal environment for the desired biological process to take place on a large and economic scale.

When a solid material is being biotreated, the desired biological reactions typically involve the degradation, either directly or indirectly, of some undesired compound present in the solid material. To accomplish this economically, the bioreactor needs to reduce the concentration of the undesired compound to an acceptable level in an acceptable quantity (in terms of flow rate) of solid material to be treated.

In general biotreatment processes are slow, and if they are aerobic, they require large amounts of oxygen for the aerobic microorganism(s) to metabolize, either directly or indirectly, the undesired compound. Oxygen transfer, therefore, is typically a major problem for the large class of aerobic biological treatment processes available. Current aerobic bioreactor designs attempt to ensure not only that the microorganisms being used have access to the material to be biooxidized or metabolized, but also that all areas of the bioreactor have an adequate oxygen and nutrient supply, as well as maintain the correct pH and temperature, for the biological process to proceed.

Stirred tank bioreactors are used in many types of aerobic biological processes, including biooxidation of refractory sulfide gold ores and bioremediation of contaminated soils. Stirred tank bioreactors provide very good contact between the bioleachant and the solid material to be treated. In addition, stirred tank processes typically have favorable oxygen conditions because the tank is sparged with air or oxygen. However, even in stirred tank bioreactors where oxygen is provided by air or oxygen sparging, the low solubility of oxygen in water (10 ppm) requires a large gas-water interface. This is generally achieved with impellers and significant expenditures of energy. The high energy costs associated with stirring and aerating the reactor make this type of bioreactor primarily applicable to bioprocesses that come to a desired end point relatively quickly, typically less than a week. For slower biological processes, a low energy cost, large scale, generally static batch process, is the best solution. However, the goal of providing the bacteria, or other microorganism, with an optimal environment is still of primary importance.

There are three primary types of static batch bioreactors used to biotreat soils contaminated with toxic organic compounds. One of these methods is landfarming. This is an above grade treatment of contaminated soil in a large open space. The soil is spread over a high-density polyurethane lined area generally covered with sand to allow for drainage. Air can be introduced by perforated pipes and by tilling the soil once or twice a week. This method has been widely implemented at sites contaminated with polynuclear aromatic (PNA's) and pentachlorophenol (PCP). One limitation of this process is that a large area is needed because the soil is spread relatively thinly to ensure adequate air flow. This method also requires tilling and may be limiting in air if the layer of soil is too thick or does not mix well.

Another technology used in the bioremediation of contaminated soil is composting. The compost is made up of contaminated soil and various amendments necessary for composting to be sustained such as wood chips, straw, or manure. These amendments increase the amount of biodegradable organics, structurally improve the compost matrix by reducing bulk weight and increasing air voids, and increase the amount of inorganic nutrients in the mixture. The composting can be carried out in a vessel with forced air flow or in open piles that are aerated by air pipes or by tilling. One disadvantage to the addition of organic amendments is that their biodegradation generates heat and requires oxygen. Composting is usually run in batch mode and a portion of the compost is used to inoculate the next compost. This process has been used effectively on many types of organic contaminates including diesel fuel, 2,4,6 trinitrotoluene (TNT), polyaromatic hydrocarbons (PAH), benzene, and xylene.

Heap bioremediation is another static bioprocess used in the bioremediation of excavated contaminated soil. In this process the soil is placed in piles 8 to 12 feet high over a lined area. To improve air flow, air can be introduced by perforated pipes. In such circumstances, the pipes are placed on approximately a 12 inch bed of the contaminated soil in regular intervals. The pipes are then typically covered with a layer of gravel to protect them from the heavy equipment. The excavated soil is then dumped in an 8 to 12 foot high pile on top of the gravel. Moisture is maintained with an irrigation system. The soil may need fertilizer or lime to adjust pH and may need sand to increase porosity. This process is low cost and thus is applicable to slow biological processes. However, this process may be too slow if the heap becomes air limited due to compaction of the soil during or after pile construction.

Therefore, air and liquid access remain important rate limiting considerations in existing static batch bioprocesses used for soil remediation, such as heap pile bioremediation, composting and landfarming. Air flow is improved in existing processes to the extent possible by introducing air through perforated air pipes or by tilling the soil. However, any flow constriction within the bioreactor will interfere with the efficiency of the process. Also, if parts of the contaminated soil are not exposed to bacteria or other nutrients as well as oxygen, the overall bioprocess will be slowed or not proceed to completion. Similarly, in the case of heap biooxidation of coal and refractory sulfide gold ore, biooxidation of the sulfides is efficiently carried out by the bacteria only when the metal sulfides are exposed to bacteria, water, nutrients, and air. If the sulfides are buried in the ore or in the solid pieces of coal, the biooxidation will not proceed. In addition, if air or liquid flow in the heap becomes limited, the biooxidation will also become limited. Consequently, a need exists for an improved bioreactor design that will permit the biotreatment of solid materials with improved air and fluid flow throughout the bioreactor and the solid material to be treated.

The use of acidophilic, autotrophic bacteria to biooxidize sulfide minerals in refractory sulfide ores is one biotreatment that has gained particular vigor in the last ten to twenty years.

Gold is one of the rarest metals on earth. Gold ores can be categorized into two types: free milling and refractory. Free milling ores are those that can be processed by simple gravity techniques or direct cyanidation. Refractory ores, on the other hand, are not amenable to conventional cyanidation treatment. Gold bearing deposits are deemed refractory if they cannot be economically processed using conventional cyanide leaching techniques because insufficient gold is solubilized. Such ores are often refractory because of their excessive content of metallic sulfides (e.g., pyrite and arsenopyrite) and/or organic carbonaceous matter.

A large number of refractory ores consist of ores with a precious metal such as gold occluded in iron sulfide particles or other metal sulfide particles. The iron sulfide particles consist principally of pyrite and arsenopyrite. Precious metal values are frequently occluded within the sulfide mineral. For example, gold often occurs as finely disseminated sub-microscopic particles within a refractory sulfide host of pyrite or arsenopyrite. If the gold, or other precious metal, remains occluded within the sulfide host, even after grinding, then the sulfides must be oxidized to liberate the encapsulated precious metal values and make them amenable to a leaching agent (or lixiviant); thus, the sulfide oxidation process reduces the refractory nature of the ore.

A number of processes for oxidizing the sulfide minerals to liberate the precious metal values are well known in the art. These methods can generally be broken down into two types: mill operations and heap operations. Mill operations are typically expensive processes having high operating and capital costs. As a result, even though the overall recovery rate is typically higher for mill type processes, mill operations are typically not applicable to low grade ores, that is ores having a gold concentration less than approximately 0.07 oz/ton. Mill operations are even less applicable to ores having a gold concentration as low as 0.02 oz/ton.

Two well known methods of oxidizing sulfides in mill type operations are pressure oxidation in an autoclave and roasting.

Oxidation of sulfides in refractory sulfide ores can also be accomplished using acidophilic, autotrophic microorganisms, such as *Thiobacillus ferrooxidans, Sulfolobus, Acidianus* species and facultative-thermophilic bacteria in a microbial pretreatment. These microorganisms utilize the oxidation of sulfide minerals as an energy source during metabolism. During the oxidation process, the foregoing microorganisms oxidize the iron sulfide particles to cause the solubilization of iron as ferric iron, and sulfide, as sulfate ion.

If the refractory ore being processed is a carbonaceous sulfide ore, then additional process steps may be required following microbial pretreatment to prevent preg-robbing of the aurocyanide complex or other precious metal-lixiviant complexes by the native carbonaceous matter upon treatment with a lixiviant.

As used herein, sulfide ore or refractory sulfide ore will be understood to also encompass refractory carbonaceous sulfide ores.

A known method of bioleaching carbonaceous sulfide ores is disclosed in U.S. Pat. No. 4,729,788, issued Mar. 8, 1988, which is hereby incorporated by reference. According to the disclosed process, thermophilic bacteria, such as *Sulfolobus* and facultative-thermophilic bacteria, are used to oxidize the sulfide constituents of the ore. The bioleached ore is then treated with a blanking agent to inhibit the preg-robbing propensity of the carbonaceous component of the ore. The precious metals are then extracted from the ore using a conventional lixiviant of cyanide or thiourea.

Another known method of bioleaching carbonaceous sulfide ores is disclosed in U.S. Pat. No. 5,127,942, issued Jul. 7, 1992, which is hereby incorporated by reference. According to this method, the ore is subjected to an oxidative bioleach to oxidize the sulfide component of the ore and liberate the precious metal values. The ore is then inoculated with a bacterial consortium in the presence of nutrients therefor to promote the growth of the bacterial consortium, the bacterial consortium being characterized by the property of deactivating the preg-robbing propensity of the carbonaceous matter in the ore. In other words, the bacterial consortium functions as a biological blanking agent. Following treatment with the microbial consortium capable of deactivating the precious-metal-adsorbing carbon, the ore is then leached with an appropriate lixiviant to cause the dissolution of the precious metal in the ore.

Oxidation of refractory sulfide ores using microorganisms, or as it is often referred to, biooxidation, can be accomplished in a mill process or a heap process. Compared to pressure oxidation and roasting, biooxidation processes are simpler to operate, require less capital, and have lower operating costs. Indeed, biooxidation is often chosen as the process for oxidizing sulfide minerals in refractory sulfide ores because it is economically favored over other means to oxidize the ore. However, because of the slower oxidation rates associated with microorganisms when compared to chemical and mechanical means to oxidize sulfide refractory ores, biooxidation is often the limiting step in the mining process.

One mill type biooxidation process involves comminution of the ore followed by treating a slurry of the ore in a stirred bioreactor where microorganisms can use the finely ground sulfides as an energy source. Such a mill process was used on a commercial scale at the Tonkin Springs mine. However, the mining industry has generally considered the Tonkin Springs biooxidation operation a failure. A second mill type biooxidation process involves separating the precious metal bearing sulfides from the ore using conventional sulfide concentrating technologies, such as floatation, and then oxidizing the sulfides in a stirred bioreactor to alleviate their refractory nature. Commercial operations of this type are in use in Africa, South America and Australia.

Biooxidation in a heap process typically entails forming a heap with crushed refractory sulfide ore particles and then inoculating the heap with a microorganism capable of biooxidizing the sulfide minerals in the ore. After biooxidation has come to a desired end point, the heap is drained and washed out by repeated flushing. The liberated precious metal values are then ready to be leached with a suitable lixiviant.

Typically precious metal containing ores are leached with cyanide because it is the most efficient leachant or lixiviant for the recovery of the precious metal values from the ore. However, if cyanide is used as the lixiviant, the heap must first be neutralized.

Because biooxidation occurs at a low, acidic pH while cyanide processing must occur at a high, basic pH, heap biooxidation followed by conventional cyanide processing is inherently a two step process. As a result, processing options utilizing heap biooxidation must separate the two steps of the process. This is conventionally done by separating the steps temporally. For example, in a heap biooxidation process of a refractory sulfide gold ore, the heap is first biooxidized and then rinsed, neutralized and treated with cyanide. To accomplish this economically and practically, most heap biooxidation operations use a permanent heap pad in one of several ore on-ore off configurations.

Of the various biooxidation processes available, heap biooxidation has the lowest operating and capital costs. This makes heap biooxidation processes particularly applicable to low grade or waste type ores, that is ores having a gold (or an equivalent precious metal value) concentration of less than about 0.07 oz/ton. Heap biooxidation, however, has very slow kinetics compared to mill biooxidation processes. Heap biooxidation typically requires many months in order to oxidize the sulfide minerals in the ore sufficiently to permit the gold or other precious metal values to be recovered in sufficient quantities by subsequent cyanide leaching for the process to be considered economical. Heap biooxidation operations, therefore, become limited by the length of time required for sufficient biooxidation to occur to permit the economical recovery of gold. The longer the time required for biooxidation the larger the permanent pad facilities and the larger the necessary capital investment. At mine sites where the amount of land suitable for heap pad construction is limited, the size of the permanent pad can become a limiting factor in the amount of ore processed at the mine and thus the profitability of the mine. In such circumstances, rate limiting conditions of the biooxidation process become even more important.

The rate limiting conditions of the heap biooxidation process include inoculant access, nutrient access, air or oxygen access, toxins build up, and carbon dioxide access, which are required to make the process more efficient and thus an attractive treatment option. Moreover, for biooxidation, the induction times concerning biooxidants, the growth cycles, the biocide activities, viability of the bacteria and the like are important considerations because the variables such as accessibility, particle size, settling, compaction and the like are economically irreversible once a heap has been constructed. This is because heaps cannot be repaired once formed, except on a limited basis.

Ores that have a high clay and/or fines content are especially problematic when processing in a heap leaching or heap biooxidation process. The reason for this is that the clay and/or fines can migrate through the heap and plug channels of air and liquid flow, resulting in puddling; channeling; nutrient-, carbon dioxide-, or oxygen-starving; uneven biooxidant distribution, and the like. As a result, large areas of the heap may be blinded off and ineffectively leached. This is a common problem in cyanide leaching and has lead to processes of particle agglomeration with cement for high pH cyanide leaching and with polymers for low pH bioleaching. Polymer agglomerate aids may also be used in high pH environments, which are customarily used for leaching the precious metals, following oxidative bioleaching of the iron sulfides in the ore.

Biooxidation of refractory sulfide ores is especially sensitive to blocked percolation channels by loose clay and fine material because the bacteria need large amounts of air or oxygen to grow and biooxidize the iron sulfide particles in the ore. Air flow is also important to dissipate heat generated by the exothermic biooxidation reaction, because excessive heat can kill the growing bacteria in a large, poorly ventilated heap.

The methods disclosed in U.S. Pat. No. 5,246,486, issued Sep. 21, 1993, and U.S. Pat. No. 5,431,717, issued on Jul. 11, 1995 to William Kohr, both of which are hereby incorporated by reference, are directed to increasing the efficiency of the heap biooxidation process by ensuring good fluid flow (both gas and liquid) throughout the heap.

Ores that are low in sulfide or pyrite, or ores that are high in acid consuming materials such as calcium carbonate or other carbonates, may also be problematic when processing in a heap biooxidation. The reason for this is that the acid generated by these low pyrite ores is insufficient to maintain a low pH and high iron concentration needed for bacteria growth.

Solution inventory and solution management also pose important rate limiting considerations for heap biooxidation processes. The solution drained from the biooxidation heap will be acidic and contain bacteria and ferric ions. Therefore, this solution can be used advantageously in the agglomeration of new ore or by recycling it back to the top of the heap. However, toxic and inhibitory materials can build up in this off solution. For example, ferric ions, which are generally a useful aid in pyrite leaching, are inhibitory to bacteria growth when their concentration exceeds about 30 g/L. Other metals that retard the biooxidation process can also build-up in this solution. Such metals that are often found in refractory sulfide ores include arsenic, antimony, cadmium, lead, mercury, and molybdenum. Other toxic metals, biooxidation byproducts, dissolved salts and bacterially produced material can also be inhibitory to the biooxidation rate. When these inhibitory materials build up in the off solution to a sufficient level, recycling of the off solution becomes detrimental to the rate at which the biooxidation process proceeds. Indeed, continued recycling of an off solution having a sufficient build-up of inhibitory materials will stop the biooxidation process altogether.

The method disclosed in U.S. patent application Ser. No. 08/329,002, filed Oct. 25, 1994, by Kohr, et al., hereby incorporated by reference, teaches a method of treating the bioleachate off solution to minimize the build-up of inhibitory materials. As a result, when the bioleachate off solution is recycled to the top of the heap, the biooxidation rate within the heap is not slowed, or it will be slowed to a lesser degree than if the off solution were recycled without treatment.

While the above methods have improved the rate at which heap biooxidation processes proceed, heap biooxidation still takes much longer than a mill biooxidation process such as a stirred bioreactor. Yet, as pointed out above, with low grade refractory sulfide ores, a stirred bioreactor is not a viable alternative due to its high initial capital cost and high operating costs. A need exists, therefore, for a heap bioleaching technique that can be used to biooxidize precious metal bearing refractory sulfide ores and which provides improved air and fluid flow within the heap. In addition, a need exists for a heap bioleaching process in which ores that are low in sulfide minerals, or ores that are high in acid consuming materials such as calcium carbonate, may be processed.

A need also exists for a biooxidation process that can be used to liberate occluded precious metals in concentrates of refractory sulfide minerals. Mill processes that are currently used for oxidizing such concentrates include bioleaching in a stirred bioreactor, pressure oxidation in an autoclave, and roasting. These mill processes oxidize the sulfide minerals in the concentrate relatively quickly, thereby liberating the entrapped precious metals. However, unless the concentrate has a high concentration of gold, it does not economically justify the capital expense or high operating costs associated with these processes. And, while a mill bioleaching process is the least expensive mill process in terms of both the initial capital costs and its operating costs, it still does not justify processing concentrates having less than about 0.5 oz. of gold per ton of concentrate, which typically requires an ore having a concentration greater than about 0.07 oz. of gold per ton. Therefore, a need also exists for a process that can be used to biooxidize concentrates of precious metal bearing refractory sulfide minerals at a rate comparable to a stirred tank bioreactor, but that has capital and operating costs more comparable to that of a heap bioleaching process.

In addition to concentrates of precious metal bearing sulfide minerals, there are many sulfide ores that contain metal sulfide minerals that can potentially be treated using a biooxidation process. For example, many copper ores contain copper sulfide minerals. Other examples include zinc ores, nickel ores, and uranium ores. Biooxidation could be used to cause the dissolution of metal values such as copper, zinc, nickel and uranium from concentrates of these ores. The dissolved metal values could then be recovered using known techniques such as solvent extraction, iron cementation, and precipitation. However, due to the sheer volume of the sulfide concentrate formed from sulfide ores, a stirred bioreactor would be prohibitively expensive, and standard heap operations would simply take too long to make it economically feasible to recover the desired metal values. A need also exists, therefore, for an economical process for biooxidizing concentrates of metal sulfide minerals produced from sulfide ores to thereby cause the dissolution of the metal values so that they may be subsequently recovered from the bioleachate solution.

Therefore, while a need exists for a method of biooxidation that can be used to process sulfide concentrates from refractory sulfide ores at a rate which is much faster than that of existing heap biooxidation processes, yet which has initial capital costs and operating costs less than that of a stirred bioreactor, this need has gone unfulfilled. Further, while a need has also existed for a method of biooxidation that can be used to economically process sulfide concentrates of metal sulfide type ores, this need has also gone unfulfilled.

SUMMARY

The present invention is directed to the biotreatment of solid materials in a nonstirred bioreactor. To this end, in a first aspect of the present invention, a method of biotreating a solid material to remove an undesired compound using a nonstirred surface bioreactor is provided. According to the method the surface of a plurality of coarse substrates is coated with a solid material to be biotreated to form a plurality of coated coarse substrates. A nonstirred surface reactor is then formed by stacking the plurality of coated coarse substrates into a heap or placing the plurality of coated coarse substrates into a tank so that the void volume of the reactor is greater than or equal to about 25%. The reactor is inoculated with a microorganism capable of degrading the undesired compound in the solid material, and the solid material is then biotreated in the surface bioreactor until the undesired compound in the solid material is degraded to a desired concentration. To ensure adequate void volume in the bioreactor, the coarse substrates preferably have a particle size greater than about 0.3 cm and the solid material to be biotreated preferably has a particle size less than about 250 μm. The thickness of the solid material coating on the plurality of coarse substrates is preferably less than about 1 mm to ensure that the microorganism being used in the biotreatment have adequate access to all of the solid material being biotreated. Thicker coatings will increase the capacity of the bioreactor, but the rate at which the biotreatment process advances will be slowed due to the limited access of the microorganism being used to the underlying particles of solid material. To make full use of the capacity of the bioreactor while ensuring adequate microorganism access, the thickness of the solid material coating should be greater than about 0.5 mm and less than about 1 mm. For enhanced air and liquid access, the void volume of the bioreactor can be set to greater than or equal to about 35%. This will greatly improve the rate at which the biotreatment process proceeds.

A variety of materials can be used for the coarse substrates, including rock, gravel, lava rock, barren rock containing carbonate minerals, brick, cinder block, slag, and plastic.

The process according to the first aspect of the invention is useful for many different biotreatment processes, including the bioremediation of contaminated soils, the desulfurization of coal, and the biooxidation of refractory sulfide ores. In bioremediation applications, the undesired compound is typically an organic compound. In coal desulfurization and refractory sulfide ore biooxidation applications, the undesired compound is sulfide minerals.

In a second aspect of the present invention, a method of biooxidizing sulfide minerals using a nonstirred surface bioreactor to liberate metal values of interest is provided. The method comprises obtaining a concentrate of metal sulfide particles from the sulfide ore body to be biooxidized and then coating the concentrate of metal sulfide particles onto a plurality of substrates, such as coarse ore particles, lava rock, gravel, or rock containing carbonate minerals as a source of $CO_2$ for the bacteria. After the metal sulfide particles are coated or spread onto the plurality of substrates, a heap is formed with the coated substrates or the coated substrates are placed within a tank. The metal sulfide particles on the surface of the plurality of coated substrates are then biooxidized to liberate the metal values of interest.

Depending on the particular ore deposit being mined, the sulfide mineral concentrates used in this invention may comprise sulfide concentrates from precious metal bearing refractory sulfide ores or they may comprise sulfide concentrates from base metal sulfide type ores, such as chalcopyrite, millerite or sphalorite. The distinction being that in the former, the metal of interest is a precious metal occluded within the sulfide minerals, and in the latter, the metal to be recovered is a base metal such as copper, nickel, or zinc and is present as a metal sulfide in the sulfide concentrate.

In a third aspect of the present invention, a method of recovering precious metal values from precious metal bearing refractory sulfide ore using a nonstirred surface bioreactor is provided. The method according to this aspect of the invention comprises the steps of producing a concentrate of metal sulfide particles from the refractory sulfide ore, coating the surface of a plurality of substrates with the concentrate of metal sulfide particles, forming a heap using the plurality of coated substrates, biooxidizing the metal sulfide particles on the surface of the plurality of substrates, contacting the biooxidized metal sulfide particles with a precious metal lixiviant to thereby dissolve precious metal values from the biooxidized metal sulfide particles, and recovering precious metal values from the lixiviant.

According to a fourth aspect of the present invention, a method of recovering precious metal values from precious metal bearing refractory sulfide ore using a nonstirred surface bioreactor is provided. The method according to this aspect of the invention comprises the steps of producing a concentrate of metal sulfide particles from a precious metal bearing refractory sulfide ore, coating the surface of a plurality of coarse substrates with the concentrate of metal sulfide particles, placing the plurality of coated substrates in a tank, biooxidizing the metal sulfide particles on the surface of the plurality of coarse substrates, contacting the biooxidized metal sulfide particles with a precious metal lixiviant to thereby dissolve precious metal values from the biooxidized metal sulfide particles, and recovering precious metal values from the lixiviant.

According to a fifth aspect of the present invention, a method for recovering metal values from a sulfide mineral ore using a nonstirred surface bioreactor is provided. The method according to this aspect of the invention comprises the steps of: producing a concentrate of metal sulfide particles from the sulfide mineral ore, coating the surface of a plurality of coarse substrates with the concentrate of metal sulfide particles, forming a heap with the plurality of coated substrates or placing the coated substrates into a tank, biooxidizing the metal sulfide particles on the surface of the plurality of coarse substrates to thereby cause the production of a bioleachate off solution, recovering the desired metal values from the bioleachate off solution. Ores of particular interest that can be processed using this process include sulfide ores of copper, zinc, nickel, molybdenum, cobalt, and uranium.

The above and other objects, features and advantages will become apparent to those skilled in the art from the following description of the preferred embodiments.

DETAILED DESCRIPTION

Figure 1:
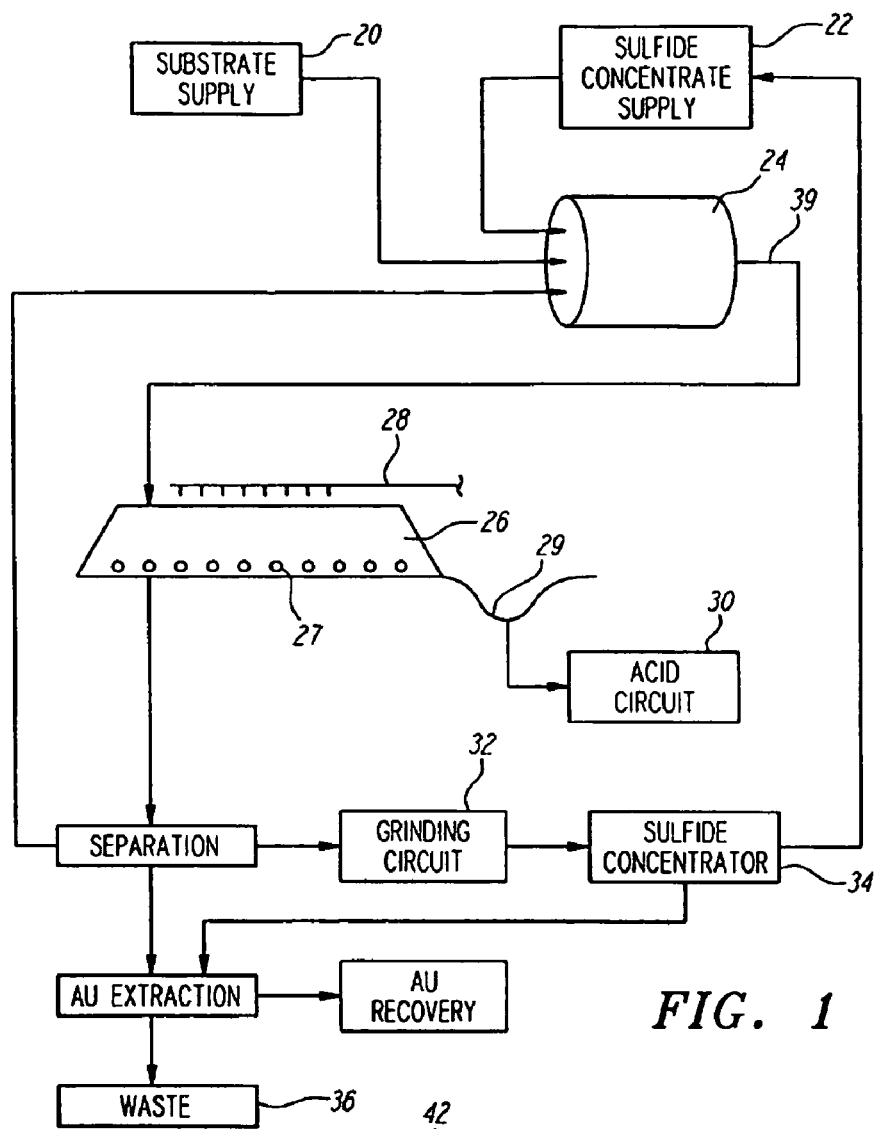
FIG. 1 is a schematic illustration of a process flow chart according to one embodiment of the present invention.

A first embodiment of the invention is now described in which a solid material is biotreated in a nonstirred surface bioreactor in order to remove an undesired compound. According to the first embodiment, the surface of a plurality of coarse substrates having a particle size greater than about 0.3 cm is coated with the solid material to be biotreated to form a plurality of coated coarse substrates. The solid material to be biotreated has a particle size of less than about 250 μm so that it forms a fairly uniform coating on the coarse substrates. A nonstirred surface reactor is then formed by stacking the plurality of coated coarse substrates into a heap or placing the plurality of coated coarse substrates into a tank so that the void volume of the reactor is greater than or equal to about 25%. The reactor is inoculated with a microorganism capable of degrading the undesired compound in the solid material, and the solid material is then biotreated in the surface bioreactor until the undesired compound in the solid material is degraded to a desired concentration.

The biotreatment process can be used in the bioremediation of contaminated soils, the desulfurization of coal, and the biooxidation of refractory sulfide ores to name a few. In bioremediation applications, the solid material is typically soil and the undesired compound is typically an organic compound within the soil. The present invention, therefore, has application at many of the existing superfund sites. A partial list of the organic contaminants which can be removed from soil using the present invention include: waste oil, grease, jet fuel, diesel fuel, crude oil, benzene, toluene, ethylbenzene, xylene, polyaromatic hydrocarbons (PAH), polynuclear aromatics (PNAs), pentachlorophenol (PCP), polychlorinated biphenyls (PCBs), creosote, pesticides, 2,4,6-trinitrotoluene (TNT), hexahydro-1,3,5-trinitro-1,3,5-triazine (RDX), octahydro-1,3,5,7-tetranitro-1,3,5,7-tetrazocine (HMX), N-methyl-N-2,4,6-tetranitroaniline, and nitrocellulose (NC).

If, on the other hand, the present invention is used to desulfurize coal, the solid material will be comprised of coal particles and the undesired compound will be the sulfide mineral particles contained within the coal particles. In refractory sulfide ore biooxidation applications, the solid material will typically be ground ore or a sulfide concentrate produced from the ore and the undesired compound will be the metal sulfide particles within the ore or concentrate.

In some instances it may be beneficial to form a concentrate by flotation or by other means where by the fraction of the solid material to be biotreated is concentrated in a smaller weight fraction. This concentrate, if it contains the majority of the undesired metal sulfides or toxins, for example, can be processed more cost effectively than the entire material.

As those skilled in the art will appreciate from the foregoing and the ensuing description, the process according to the present invention has broad applicability in that it can be used to biotreat any solid material that contains an undesired compound which is susceptible to biodegradation or biooxidation by a microorganism or the enzymes produced by a microorganism.

The purpose of the coarse substrates is to provide a support with a relatively large surface area upon which the solid material to be biotreated can reside during the biotreatment process. Therefore, when a large number of coated coarse substrates are stacked in a heap or placed in a tank, a nonstirred surface reactor is formed that has a very large active surface area per cubic meter of reactor space. Although the exact surface area of the reactor per cubic meter of reactor space will depend on the particular size of the coarse substrates employed, it should be at least 100 square meters per cubic meter of reactor and will typically be 500 square meters or more per cubic meter of reactor space. Furthermore, by using coarse substrates that have a particle size greater than about 0.3 cm and restricting the particle size of the solid material to be biotreated to less than about 250 µm, the reactor will be ensured adequate void volume to permit air and nutrients to access all parts of the reactor during the biotreatment process. In this regard, the void volume of the reactor should be at least about 25%. Such a void volume will also ensure adequate heat dissipation within the heap. For enhanced air and liquid access and heat dissipation, the void volume of the bioreactor can be set to greater than or equal to about 35%. This will greatly improve the rate at which the biotreatment process proceeds.

While using larger coarse substrates will increase the void volume in the reactor and thus improve air and nutrient access, in addition to heat dissipation, throughout the entire reactor, the use of larger substrates reduces the loading capacity of the bioreactor. A good compromise between ensuring adequate void volume and ensuring adequate reactor capacity can be achieved by using coarse substrates having a nominal particle size that is greater than about 0.6 cm and less than about 2.54 cm.

A variety of materials can be used for the coarse substrates, including rock, gravel, lava rock, barren rock containing carbonate minerals, brick, cinder block, slag, and plastic. Lava rock is particularly preferred because of its rough, nonuniform surface, thus increasing its surface area for a given particle size substrate and improving the integrity of the coating of solid material which is applied to it. Coarse barren rock containing carbonate minerals is advantageous if the biotreatment process is acidic because the acid will react with the carbonate minerals to slowly cause the release of carbon dioxide, which autotrophic microorganisms can use as a source of carbon to carry out metabolic synthesis. The carbon dioxide production can thus be used to promote microorganism growth in the reactor.

When a refractory sulfide ore or sulfide concentrate is being biooxidized to reduce the sulfide mineral content therein, coarse ore particles can be used as the coarse substrates. Similarly, if the process is being used to desulfurize coal, coarse coal particles can be used as the coarse substrates. In both cases, the substrate may benefit from the biooxidation process carried out on its surface.

While the coarse substrates have been defined as having a particle size of greater than about 0.3 cm, it is recognized and contemplated that some of the coarse substrate material may actually be smaller than this. As those skilled in the art will recognize that if the coarse substrates are produced by crushing lager material to the desired size range, the crushed material will have a certain size distribution. And, even if the material is screened to exclude material less than about 0.3 cm, some material having a particle size less than the 0.3 cm target minimum will still be present in the coarse substrates due to inherent inefficiencies in the screening process and due to particle attrition during handling. Thus, by greater than about 0.3 cm it is intended that substantially all of the coarse substrates are above this size so that the void volume of the reactor remains above at least about 25% during formation of the reactor and throughout its operation. Preferably the amount of coarse substrates below the 0.3 cm cutoff is less than 5% by weight.

In general, the solid material to be biotreated should be much smaller than the coarse substrate onto which it is coated. This material should be ground to a small enough size to allow the microorganism employed in the biotreatment to have access to all the material so that the undesired compound can be biooxidized or biodegraded in a time that is generally larger than a stirred tank process, but shorter than a heap process of the whole material. This time will generally be between 14 days and 90 days, depending on the undesired compound and the rate of its biodegradation or biooxidation.

The maximum solid material particle size has been set at about 250 µm so that the solid material will form a relatively uniform coating on the coarse substrates during the coating process, rather than forming agglomerates between themselves. Furthermore, particles larger than 250 µm may not adhere to the surface of the coarse substrates very well without the use of a binder.

It is desirable to form a relatively uniform coating of the fine particles on the coarse substrates during the coating process because this will maximize the integrity of the coating and the surface area of the solid material exposed to the active microorganism which is added to the bioreactor. If agglomerates of the solid material are formed during the coating process, the particles of solid material which are in the interior of the agglomerate will be blocked from the action of the microorganism and thus the amount of biological treatment they will receive will be reduced or nonexistent. Further, the agglomerates are not as structurally sound as the coated substrates and are likely to break apart during the stacking process used to form the reactor or during biotreatment, potentially leading to the formation of blockages within the reactor, which could blind off portions of the reactor from the biological treatment.

Typically as the particle size of the solid material to be biotreated decreases, the biotreatment process will proceed faster and more solid material can be loaded onto the coarse substrates. Smaller particle sizes will also tend to stick better to the surface of the coarse substrates. If the particle size of the solid material to be treated is less than about 25 µm, however, excessive dust problems could be encountered during handling and some clumping may be experienced during the coating process.

Preferably the particle size of the solid material to be treated has a nominal particle size which is greater than about 75 µm and less than about 106 µm. Particles in this size range will adhere well to the coarse substrates, and the incremental improvements which can be achieved in the rate of the biotreatment process with finer particle sizes are rarely justified by the added grinding costs of producing them.

The coated substrates can be produced by adding the coarse substrates and solid material to a rotating drum in appropriate quantities. Preferably the coarse substrates are dry and the solid material is in a high pulp density slurry so that it will stick to the coarse substrates as the slurry coats the coarse substrates. Alternatively, both the coarse substrates and solid material can be dry when added to the rotating drum and water sprayed into the drum to promote adhesion of the solid material to the coarse substrates. In forming the coated substrates, it is desirable to maintain the moisture content of the solid material within the range of 5 to 30 weight % to promote proper adhesion between the solid material and coarse substrates.

As those skilled in the art will recognize many other techniques can also be used to coat the coarse substrates. For example, the solid material to be biotreated can be sprayed in a high pulp density slurry form onto the coarse substrates as the plurality of coarse substrates are being stacked to form the reactor.

If the solid material to be biotreated is applied as a slurry, adjustments can be made to the material to optimize the biotreatment process. For example, the pH can be adjusted to the optimum pH range for the microorganism that is to be used to break down the undesired compound. If nutrients, amendments, or inoculants are needed, they can also be added at this time. In some cases it may be advantageous to start the bioprocess in a tank prior to application of the particles of solid material to the coarse substrates.

The integrity of the coated coarse substrates should be sufficient enough to prevent a large number of blockages from forming in the flow channels of the reactor while the particles of solid material on the surface of the coated substrates are being biotreated. Such blockages will decrease oxygen flow and microorganism migration within the bioreactor and thereby reduce the rate of the biotreatment process. Of course, the larger the coarse substrates are in relation to the particle size of the solid material, the less likely such blockages will form because the solid material will be much smaller than the interstices between the coarse substrates. The integrity of the coated substrates should also be sufficient enough to prevent excessive amounts of the solid material from washing from the bioreactor during the biotreatment process.

Although the surface tension of water should hold the particles of solid material to the surface of the coarse substrates in most instances, if it is found that the particles of solid material are washing from the bioreactor in excessive concentrations or that blockages are forming in the bioreactor due to degradation of the coating, a binding agent can be used to improve the integrity of the coating. However, binding agents may interfere with the access of the biotreatment microorganism to some of the solid material to be biotreated, thus increasing the time necessary for the biotreatment process to reach the desired end point.

The thickness of the solid material coating on the plurality of coarse substrates is preferably less than about 1 mm to ensure that the microorganism being used in the biotreatment have adequate access to all of the solid material being biotreated. Thicker coatings will increase the capacity of the bioreactor, but the rate at which the biotreatment process advances will be slowed due to the limited access of the microorganism being used to the underlying particles of solid material. To make full use of the capacity of the bioreactor while ensuring adequate microorganism access, the thickness of the solid material coating should be greater than about 0.5 mm and less than about 1 mm. When a rock or brick substrate is being used, this will translate into a solid material loading of approximately 10 to 30 percent by weight.

The nonstirred surface reactor is formed by stacking a plurality of the coated substrates in a heap or in a tank. Conveyor stacking will minimize compaction of the coated substrates within the reactor. However, other means of stacking may be employed.

Preferably the reactor is inoculated with the microorganism(s) which is to be used in the biotreatment process while the plurality of coated substrates are being stacked to form the nonstirred surface reactor or immediately after formation of the reactor. Alternatively, if the microorganism(s) to be employed in the biotreatment process function best in a particular pH range, the pH of the reactor can be adjusted prior to inoculation as is well known in the art.

The microorganisms which are useful in the present biotreatment process are the same microorganisms that have traditionally been used to degrade a particular undesired compound in existing biodegradation and biooxidation processes. For example, acidophilic, autotrophic bacteria such as *Thiobacillus ferrooxidans, Leptospirillum ferrooxidans*, and *Sulfolobus*, can be used to biooxidize sulfide minerals in coal desulfurization or refractory sulfide ore biooxidation applications. Other bacteria that are useful in these applications are well within the ordinary skill of those in the art. Similarly, with respect to soil remediation applications, the microorganism(s) which should be employed are the same as those currently employed in present bioremediation processes such as composting, landfarming, slurry biodegradation, and heap pile bioremediation. Those having ordinary skill in the art will be readily able to determine which microorganism(s) are applicable for the various undesired compounds which may be removed from the solid material using the process according to the present invention.

Once the reactor is inoculated with an appropriate microorganism, the conditions such as pH, temperature, nutrient supply, and moisture content within the reactor should be monitored and maintained throughout the biotreatment so as to promote the growth of the microorganism to the fullest extent possible. As the microorganism grows throughout the reactor, the reactor is transformed into a bioreactor having a very large surface area that will biodegrade or biooxidize the undesired compound in a time much shorter than that of traditional static batch biotreatment processes such as heap bioleaching, composting, and landfarming.

The reactor can also be provided with perforated air pipes through which air can be blown or drawn as is well known in the art. Whether air is blown or drawn through the reactor will depend on the specific bioprocess occurring within the reactor, and such a selection is also well within the skill of those in the art.

The biotreatment process should be permitted to proceed until the undesired compound in the solid material is degraded to a desired concentration. In the case of soil remediation applications, this will typically be dictated by governmental regulations which define the acceptable level of a particular contaminant. In coal desulfurization applications, the amount of residual sulfur which is permitted to remain in the coal will also depend, to a large extent, on environmental regulations, because when sulfur bearing coal is burned it will produce sulfur dioxide as a byproduct. Thus, the amount of sulfur allowed to remain in the coal should be less than that which would violate environmental regulations when the coal is burned. This, of course, will depend to some extent on the equipment employed at the coal fired plant where the biotreated coal will be utilized. With respect to the biooxidation of refractory sulfide ores or concentrates, the amount of sulfide mineral that is permitted to remain in the ore will be dictated by the amount that must be biooxidized to achieve economical recoveries of the desired metal values from the ore or concentrate.

After the undesired compound has been reduced to a desired concentration, the bioreactor can be broken down and the biotreated solid material separated from the coarse substrates. After separation of the biotreated solid material, the coarse substrates can be reused. After one or more uses in the biotreatment process, a film of the microorganism used in the biotreatment process will develop on the substrates. This biofilm will have the advantage of adaptation to any toxic or inhibitory materials that are present in the solid material being processed. It is therefore best to remove the biotreated solid material in such a way as to not kill or entirely remove the biofilm that has built up on the coarse substrates. The biofilm is also an efficient way to inoculate the next coating of solid material applied to the coarse substrates. Finally, the adaptation of the microorganism after having been through the process many times will also speed up the rate at which the microorganism biodegrades or biooxidizes the undesired compound in the solid material being processed.

The present invention will now be described in further detail in connection with a number of possible embodiments that can be employed in the processing of refractory sulfide ores.

The second embodiment of the present invention is described in connection with FIGS. 1 and 2. FIG. 1 illustrates a process flow chart for liberating and recovering precious metal values from precious metal bearing refractory sulfide ores. For purposes of describing the process illustrated in FIG. 1, the sulfide mineral concentrate 22 used in the present embodiment is produced from a gold bearing refractory sulfide ore. It follows, therefore, that the precious metal recovered in the present embodiment is gold. However, as one skilled in the art would understand, other precious metals, such as platinum and silver, can also be liberated and recovered from refractory sulfide ores using the process illustrated in FIG. 1. A combination of precious metals can also be recovered using the process according to the present embodiment if the refractory sulfide ore body used to produce the sulfide mineral concentrate 22 contains more than one precious metal.

According to the process flow chart shown in FIG. 1, a plurality of substrates 20 and a sulfide mineral concentrate 22 are added to a rotating drum 24. Preferably the sulfide mineral concentrate 22 is in a slurry form and the plurality of substrates 20 are dry when added to rotating drum 24 to improve the adhesion between the substrates 20 and the concentrate 22. Optionally, a polymeric binding agent can be added to rotating drum 24, although it is not necessary. As rotating drum 24 rotates, the substrates 20 added to drum 24 are coated with the wet sulfide mineral concentrate 22 to form coated substrates 39. Coated substrates 39 are then stacked to form static heap 26.

By using a slurry of concentrate in the coating process, the need and cost of drying the concentrate after its production is eliminated. Concentrate 22 and the plurality of substrates 20 can, however, be added to rotating drum 24 in the dry state, in which case after the mixture is added to drum 26 it is sprayed with water or an aqueous acid solution, preferably containing ferric ions, to cause the concentrate to stick to the substrates. The benefit of using an aqueous acid solution containing ferric ions to bind the concentrate to the surface of the substrates is that it will begin to chemically oxidize the sulfide mineral concentrate. Also it is acidic so that it will lower the pH of the coated substrates 39 in preparation for biooxidation. The disadvantage of using such an acid solution is that it will increase the cost of the equipment used to form the coated substrates 39 because it must be designed to be acid resistant.

Sulfide mineral concentrate 22 is comprised of a plurality of fine metal sulfide particles 40 which have finely disseminated gold and possibly other precious metal values occluded within. Sulfide mineral concentrate 22 will also typically contain fine particles of sand or other gangue material 42 from the refractory sulfide ore from which concentrate 22 is obtained. As a result, each of the coated substrates 39 will be coated with the metal sulfide particles 40 and fines 42 as illustrated in FIG. 2.

The integrity of coated substrates 39 should be sufficient enough to prevent a large number of blockages from forming in the flow channels within heap 26 while the metal sulfide particles 40 on the surface of coated substrates 39 are being biooxidized. Such blockages decrease oxygen flow and bacteria migration within the heap and thereby reduce the rate of biooxidation.

Because metal sulfide particles 40 are hydrophobic, they will tend to stick to the dry substrates 20 without the use of a binding agent such as a polymeric agglomeration aid. This assumes, however, that the metal sulfide particles 40 are of an appropriate size. Therefore, if concentrate 22 contains an adequate concentration of metal sulfide particles 40, concentrate 22 will remain sufficiently adhered to coated substrates 39, even without the use of a binding agent, to permit coated substrates 39 to be handled while being stacked on heap 26 or placed in tank 45, which is described later in connection with the embodiment illustrated in FIG. 5. Furthermore, coated substrates 39 should retain their integrity throughout the biooxidation process. When forming coated substrates 39 without the use of a binding agent, therefore, it is important to use a sulfide mineral concentrate which has an adequate concentration of metal sulfide particles and an appropriate particle size.

While a polymeric binding agent can be used and would possibly improve the integrity of the coated substrates 39, the use of such agents will increase the operating cost of the process.

Several factors need to be taken into consideration when determining the appropriate concentration of metal sulfide particles 40 in concentrate 22. First, higher concentrations of metal sulfides are desirable in the concentrate so that more metal sulfide particles 40 can be processed per unit surface area of substrates 20. This is advantageous in that as the loading of metal sulfide particles increases, the rate of biooxidation in heap 26 will tend to increase. Furthermore, because the precious metal values are occluded within the metal sulfide particles 40, higher concentrations of these particles in concentrate 22 will tend to result in improved recovery rates for a particular ore body, in addition to lowering the cost of processing the concentrate per ounce of gold produced.

A second factor that weighs in favor of producing a concentrate 22 that contains as much metal sulfides as practicable is that the potential for the formation of blockages in the flow channels of heap 26 is reduced by minimizing the amount of gangue material 42 in concentrate 22. The reason being that the fine particles of gangue material 42 are more hydrophilic than the fine metal sulfide particles 40, and, as a result, they tend to adhere to the surface of substrate 20 less tenaciously. The fine particles of gangue material 42 will, therefore, tend to migrate through the heap with the added bioleachant maintenance fluids during biooxidation, which in turn increases the likelihood that blockages will form in flow channels of heap 26. Accordingly, as the concentration of metal sulfide particles approaches 20 weight %, it may be desirable or even necessary to use a polymeric agglomeration aid to ensure sufficient integrity of the coated substrates 39 during handling and biooxidation. On the other hand, by using a sulfide mineral concentrate with at least about 40 weight % metal sulfide particles, coated substrates 39 can be readily formed without the use of a polymeric agglomeration aid and a high degree of loading of metal sulfide particles 40 per unit surface area is achieved.

At least two factors militate against using a sulfide mineral concentrate 22 having a very high concentration of metal sulfide particles 40. First, the cost of producing concentrate 22 is typically proportional to its concentration of metal sulfide particles. Thus, as the concentration of metal sulfide particles 40 in concentrate 22 increases, the cost of producing concentrate 22 will likewise increase. The added cost of producing very high grades of concentrate 22 may not be offset by the incremental improvement in metal sulfides loading or integrity of the coated substrates 39. Second, as the grade of concentrate increases, the amount of metal sulfide particles 40 that remain with the tail fraction of the refractory sulfide ore will increase. Because these metal sulfide particles contain occluded precious metal values, any metal sulfide particles 40 that remain in the ore tail will decrease the total recovery rate for the process.

Taking the above factors into consideration, sulfide mineral concentrate 22 should contain at least 20 weight % metal sulfides to ensure adequate handling characteristics and integrity during biooxidation. Preferably, however, the concentrate will contain at least about 40 weight % metal sulfides, and more preferably at least about 70 weight %. Typically, concentrate 22 will contain between about 40 to 80 weight % metal sulfides.

In general, as the particle size of the sulfide mineral concentrate 20 decreases, the faster the biooxidation process will proceed. Smaller particle sizes also tend to result in improved concentrate grades. This is because it is typically easier to separate the metal sulfide particles 40 from the bulk of gangue material as the particle size of the ore is decreased. Sulfide mineral concentrate 22, therefore, preferably has a particle size of less than about 250 µm. Particles larger than 250 µm may not adhere to substrates 20 very well without the use of a binding agent. In addition, unless the refractory sulfide ore from which concentrate 22 is produced is ground to at least 100% passing 250 µm, it is difficult obtain a good separation of the metal sulfide particles 40 from the bulk of gangue material during concentration. This is especially true if flotation is used to form concentrate 22, because particles larger than 250 µm do not float very well. On the other hand, if the particle size of concentrate 22 is less than about 38 µm to 25 µm, the concentrate particles will tend to clump together during the coating process rather than form a relatively uniform coating on coated substrate 39. These clumps of concentrate can block air flow and bacteria migration during biooxidation, thereby reducing the rate of biooxidation in the heap.

Preferably the particle size of concentrate 22 is about 100% passing 106 µm to 75 µm. Particles in this size range adhere well to substrates 20, and the incremental improvements which can be achieved in the rate of biooxidation and the concentrate grade with finer particle sizes are rarely justified by the added grinding costs of producing them.

Sulfide mineral concentrate 22 can be produced from any precious metal bearing refractory sulfide ore body being mined using techniques well known in the art and thus need not be explained in detail here. The production of concentrate 22, however, will typically include the crushing and grinding of the refractory sulfide ore to an appropriate particle size followed by one or more gravity separations or one or more sulfide flotations.

Some potential refractory sulfide ore bodies may already be of sufficient grade such that further concentration is not required. Such ore bodies may include tailings or waste heaps at existing mines. When these types of ores are processed, the sulfide mineral concentrate need only be transported to the location of the biooxidation facility and possibly some additional comminution to achieve the desired particle size.

With respect to gold concentration, the process according to the present embodiment can be performed economically even if concentrate 22 contains as little as 5 g Au/metric ton of concentrate (or an equivalent economic value of other precious metal values). This number of course will vary to a large extent based on the cost of producing concentrate 22 and the prevailing price of gold. As those skilled in the art will recognize, however, traditional autoclaves or stirred tank bioreactors cannot come close to economically processing a sulfide mineral concentrate having such a low concentration of gold.

Many different materials can be used for substrates 20. Preferred substrates include coarse refractory sulfide ore particles, lava rock, gravel, and rock which includes a mineral carbonate component. The purpose of the substrates 20 is to provide a support with a relatively large surface area upon which the concentrate 22 can reside during the biooxidation process. The surface area of each substrate 20 in effect acts as a small surface bioreactor during biooxidation. Therefore, when a large number of coated substrates 39 are stacked in heap 26 for biooxidation, a nonstirred surface bioreactor is created that has a very large total surface area.

The total surface area of the bioreactor or heap 26 can be increased by decreasing the particle size of substrates 20, using substrates that have a rough, nonuniform surface morphology and/or increasing the number of coated substrates 39 stacked on heap 26. The advantage of increasing the total surface area of the substrates 20 within heap 26 is that the amount of concentrate 22 that can be loaded on substrates 20 increases proportionately, which in turn increases the amount of concentrate 22 that can be biooxidized in a particular heap 26.

The preferred particle size range for substrates 20 is nominally from about +0.62 cm to about −2.5 cm with particles less than about 0.3 cm removed by screening or other suitable method. However, substrates 20 having a particle size down to approximately +600 µm can be used. While increased loading is achieved with smaller substrate particle sizes, increased air flow, fluid flow and heat dissipation is achieved with larger particle sizes. The nominal +0.62 to −2.5 cm size range provides a good compromise between concentrate loading and ensuring adequate air flow, fluid flow, and heat dissipation.

Substrates 20 are preferably loaded with as much concentrate 22 during the coating process as possible to maximize the process throughput. The amount of concentrate 22 that can be loaded on substrates 20 will depend on particle size and surface morphology of the substrates 20. Coarse substrates 20 and sulfide mineral concentrate 22 should, therefore, be added to rotating drum 24 in sufficient quantities to maximize the amount of sulfide mineral concentrate 22 loaded on each substrate 39 while minimizing the formation of agglomerates of the sulfide mineral concentrate particles. Clumps or agglomerates of the sulfide mineral concentrate 22 particles may be formed if the particle size of the concentrate is too fine, as discussed above, or if an excess amount of the concentrate is added to drum 24. To ensure adequate loading of substrates 20 while simultaneously avoiding formation of agglomerates of the concentrate particles, preferably approximately 10 to 30 weight % concentrate is added to rotating drum 24, which will result in a loading of approximately 10 to 30 weight % of concentrate 22 on coated substrates 39.

In forming coated substrates 39, it is desirable to maintain the moisture content of concentrate 22 within the range of 5 to 30 weight %. If the moisture content of the concentrate is below 5 weight %, the concentrate will not adhere properly to the substrates, and if the moisture content exceeds 40 weight %, the concentrate slurry will be too thin to form a thick enough coating on the substrate. This would limit the amount of concentrate that would adhere to the substrates 20.

Although other means of heap construction may be used, conveyor stacking is preferred. Conveyor stacking minimizes compaction of the coated substrates within the heap. Other means of stacking such as end dumping with a dozer or top dumping can lead to regions of reduced fluid flow within the heap due to increased compaction and degradation of the coated substrates.

If desired, heap 26 can be provided with perforated pipes 27 connected to an air supply source (not shown) in order to increase the air flow within the heap. Increasing the air flow within heap 26 will increase the rate of biooxidation and improve the rate at which heat is dissipated from the heap. Furthermore, because of the large air and fluid flow channels between the coated substrates 39, the air supply source connected to perforated pipes 27 can be a low cost blower rather than a more expensive compressor.

Heap 26 is preferably inoculated with a bacteria capable of biooxidizing metal sulfide particles 40 while coated substrates 39 are being stacked on to heap 26 or immediately after formation of heap 26 or after the pH of heap 26 has been lowered to below 2.5. The following bacteria may be used in the practice of the present invention:

*Thiobacillus ferrooxidans; Thiobacillus thiooxidans; Thiobacillus organoparus; Thiobacillus acidophilus; Leptospirillum ferrooxidans; Sulfobacillus thermosulfidooxidans; Sulfolobus acidocaldarius; Sulfolobus BC; Sulfolobus solfataricus* and *Acidianus brierleyi* and the like.

These bacteria are all available from the American Type Culture Collection or like culture collections. Whether one or more of the above bacteria and the particular bacteria selected for use in the present process will depend on factors such as the type of ore being processed and the expected temperatures in heap 26 during biooxidation. These selection criteria, however, are well within the skill of those in the art and need not be described in detail here. The most common and preferred bacteria for biooxidation is *Thiobacillus ferrooxidans*.

During the biooxidation of the metal sulfide particles 40 coated on the surface of the coated substrates 39, additional inoculant and microbial nutrient solutions can be supplied through a sprinkler system 28. Additions of these bioleachant maintenance solutions will typically be made in response to certain performance indicators used to monitor the progress of the biooxidation process.

The rate of biooxidation is preferably monitored throughout the biooxidation process based on selected performance indicators such as the solubilization rate of arsenic, iron, or sulfur, or the oxidation rate of sulfides which can be calculated therefrom. Other biooxidation performance indicators that may be used include measuring pH, titratable acidity, and solution Eh. Preferably the bioleachate off solution that percolates through the heap is collected at drain 29 and recycled to the top of heap 26. This minimizes the amount of fresh water required by the biooxidation process. And, because the bioleachate off solution will be acidic and contain a high concentration of ferric ions, its reapplication to the top of heap 26 is advantageous to the biooxidation process. However, the effluent solution generated early in the biooxidation process will also contain significant concentrations of base and heavy metals, including components that lead to microbial inhibition. As the inhibitory materials build-up in the bioleachate off solution, the biooxidation process is retarded. Indeed, continued recycling of an off solution without treatment can lead to a build-up of inhibitory materials sufficient to stop the biooxidation process altogether.

To minimize the build-up of inhibitory materials and thus their effect on the biooxidation process, the off solution can be treated in acid circuit 30 prior to recycling to remove the inhibitory materials when their concentration becomes excessive. One method of conditioning the bioleachate off solution before recycling comprises raising its pH above 5, removing any precipitate that forms and then lowering its pH to a pH appropriate for biooxidation using an untreated portion of the off solution or other acid solution. Such a conditioning process is disclosed in U.S. patent application Ser. No. 08/547,894, filed Oct. 25, 1995 by Kohr et al, which is hereby incorporated by reference.

The bioleachate off solution will tend to be very acidic in the present invention. This is because a concentrate having a relatively high concentration of metal sulfide minerals is being biooxidized rather than an entire ore. As a result, the biooxidation process according to the present invention will tend to produce large amounts of excess acid. That is the process will produce more acid than can be practically recycled to the top of heap 26. This excess acid must be disposed of or used for other purposes. One possible use for the excess acid is in a copper oxide ore leaching process because sulfuric acid is an effective lixiviant for copper oxide ores. However, the sulfuric acid solution produced as a byproduct of the present process will also typically contain a high concentration of ferric ions. This also makes it an effective lixiviant for some copper sulfide ores such as chalcocite. The ferric ion in the acid solution chemically oxidizes the copper sulfide minerals to cause their dissolution. Thus, the excess acid from the present process can be beneficially used in a copper leaching operation to avoid the neutralization costs associated with disposal while simultaneously reducing the acid costs for the copper leaching operation.

After the biooxidation reaction has reached an economically defined end point, that is after the metal sulfide particles 40 on the surface of the coarse substrates 20 are biooxidized to a desired degree, the heap is broken down and the biooxidized concentrate 22 is separated from the coarse substrates 20. Prior to breaking the heap down, however, the heap will typically be drained and then washed by repeated flushings with water. The number of wash cycles employed is typically determined by a suitable marker element such as iron and the pH of the wash effluent.

Separation can be accomplished by placing the coated substrates 39 on a screen and then spraying the coated substrates with water. Alternatively, the coated substrates can be tumbled in water using a trommel.

Following separation, gold is extracted from the biooxidized concentrate 22. This can be accomplished using a number of techniques well known in the art. Typically, however, the biooxidized concentrate will be leached with a lixiviant such as cyanide in a carbon-in-pulp or a carbon-in-leach process. In these processes, the lixiviant dissolves the liberated gold or other precious metal values that are then adsorbed onto activated carbon as is well known in the art.

If cyanide is used as the lixiviant, the concentrate will need to be neutralized prior to leaching. To avoid the need for neutralization, thiourea can be used as the lixiviant to extract the gold from the biooxidized concentrate. The thiourea extraction process can be improved by adjusting the Eh of the leach solution using sodium metabisulfite as disclosed in U.S. Pat. No. 4,561,947, which is incorporated herein by reference. If thiourea is used as the lixiviant, preferably a synthetic resin, rather than activated carbon, is used to adsorb the dissolved precious metal values from the lixiviant solution.

After the liberated gold or other precious metal values are extracted from the biooxidized concentrate, the biooxidized concentrate is taken to a waste or tailings pile 36 and gold is recovered from the carbon or synthetic resin using techniques well known in the art.

The coarse substrates 20 which have been separated from the biooxidized concentrates can be recycled to the rotating drum for a new coating of sulfide mineral concentrate 22. Substrates 20 can be reused so long as they retain their mechanical integrity. If coarse refractory sulfide ore particles are used for substrates 20, they are preferably processed at some point, preferably after one to three cycles, to recover liberated gold values.

Figure 2:
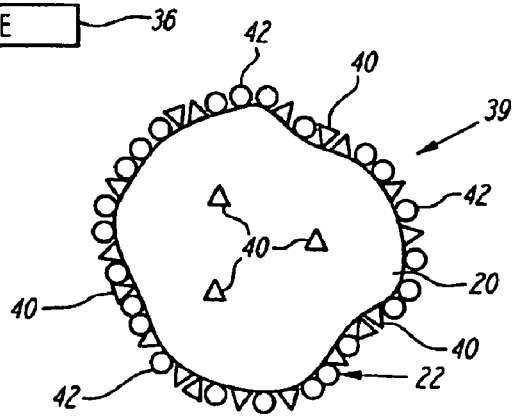
FIG. 2 is a cross sectional view of a refractory sulfide ore substrate coated with a concentrate of metal sulfide particles in accordance with the present invention.

As illustrated in FIG. 2, coarse refractory sulfide ore substrates 20 will contain metal sulfide particles 40 which contain occluded gold and other precious metal values. After one to three cycles through the process, many of the metal sulfide particles 40 within the coarse ore substrates 20 will be partially biooxidized. Rather than continuing to recycle the coarse ore substrates in this situation and allow the liberated gold values to go unclaimed, the coarse ore substrates can be processed to recover their gold values. This is preferably accomplished by grinding the coarse ore substrates in grinding circuit 32 to a particle size suitable to permit the metal sulfide particles to be separated from the bulk of the gangue material. A concentrate 22 of the metal sulfide particles 40 from the ground coarse ore substrates is then produced in the sulfide concentrator 34. Preferably sulfide concentrator 34 is a flotation cell and the biooxidized coarse ore substrates are ground to a size appropriate for sulfide flotation and coating on substrates 20. The concentrate 22 produced from the ground ore substrates is then combined with the supply of sulfide mineral concentrate 22 from which it is coated on a second plurality of coarse substrates 20 and added to a new heap 26 for further biooxidation.

The flotation tail from sulfide concentrator 34 should be treated in the gold extraction process along with the biooxidized concentrate 22 from heap 26. The flotation tail will contain a number of fully and partially oxidized metal sulfide particles that did not float. These oxidized particles will contain significant gold values, and as much of these gold values will already be liberated, they can be readily leached from the flotation tail using cyanide or thiourea. After lixiviation, the flotation tail is disposed of along with the biooxidized concentrate which has gone through gold extraction in waste or tailings pile 36.

Refractory sulfide coarse ore substrates 20 that have gone through the biooxidation process can alternatively be processed simply by grinding followed by lixiviation. This process alternative, however, will result in a lower overall recovery, because many of the metal sulfide particles 40 within the coarse ore substrates will not be sufficiently oxidized to liberate their entrapped gold values.

With respect to material selection for substrates 20, there are several advantages of using coarse refractory sulfide ore particles.

First, the refractory sulfide ore body being mined will typically have to go through several crushing and grinding steps before an appropriate particle size is achieved for producing concentrate 22. As a result, coarse refractory sulfide ore substrates can be removed from an appropriate stage of the crushing process, which makes coarse refractory sulfide ore particles an inexpensive source of substrates 20.

Second, as illustrated in FIG. 2 and discussed above, if coarse refractory sulfide ore is used as the substrate material, it will contain metal sulfide particles 40. These metal sulfide particles will be partially biooxidized during the biooxidation process, and, if the coarse ore particles are recycled through the process several times, the metal sulfide particles 40 will eventually become sufficiently biooxidized to permit recovery of their precious metal values.

A third advantage, which is somewhat related to the second, is that a fraction of the iron sulfide or other metal sulfide particles 40 in the refractory sulfide ore are so fine that they will not float very well in the concentration process. By using coarse particles of the ore for substrates 20, these very fine metal sulfide particles will be chemically oxidized over time by the ferric ion in the bioleachant. Then, when the coarse ore particles are eventually ground and floated to produce a concentrate of metal sulfide particles, the oxidized fine metal sulfide particles will end up in the flotation tails. Because the flotation tails are leached with cyanide or other lixiviant, the liberated gold values from these very fine sulfide particles will be recovered. On the other hand, if the coarse ore particles were not used as substrates 20 prior to grinding and flotation, the very fine metal sulfide particles would still end up in the flotation tails when producing concentrate 22. However, because these very fine sulfide particles would not be partially biooxidized at this point, their occluded gold values cannot be recovered by lixiviation.

A fourth advantage of using refractory sulfide coarse ore as substrates 20 is that the metal sulfide particles in the biooxidized support material will be easier to float following biooxidation. This is because the surface of the metal sulfide particles is altered during the biooxidation process. Thus, after the coarse ore support material has been reused several times and it is ground and floated to produce a sulfide mineral concentrate, improved flotation results can be achieved.

If the coarse ore particles also contain a carbonate mineral component, a fifth advantage exists for using coarse refractory sulfide ore particles as the coarse substrates 20. Carbonate minerals tend to be very acid consuming. As a result, ores which contain these minerals have traditionally required a lot of acid conditioning prior to biooxidation. Acid conditioning of these ores is required to remove or reduce the carbonate mineral component prior to biooxidation so that the biooxidation reaction can proceed. And, while coarse refractory sulfide ore particles in general tend to biooxidize very slowly—often taking up to nine months or more—if lots of carbonate minerals are included in the ore, without preconditioning, the coarse ore particles may never biooxidize. In the process according to the present invention, however, coarse refractory sulfide ore particles that contain carbonate minerals can be advantageously used for substrates 20. During the biooxidation process, the acid produced from the biooxidation of the concentrate 22 on the surface of the coarse ore substrates will slowly neutralize the carbonate minerals in the substrates. A byproduct of the neutralization process is carbon dioxide, which the autotrophic bacteria used in the present invention can use as a source of carbon to carry out metabolic synthesis. The carbon dioxide production, therefore, will promote bacteria growth in heap 26, which in turn increases the rate of biooxidation of concentrate 22. Thus, by using coarse ore that contains carbonate minerals for support material 20, the coarse ore will be slowly neutralized for future biooxidation and bacteria growth in heap 26 will be promoted. A concomitant benefit, as noted above, will be the biooxidation of the very fine nonfloatable sulfide particles that are in the coarse ore.

As those skilled in the art will recognize, the coarse refractory sulfide ore particles used for substrates 20 do not have to originate from the same ore body as that used to produce concentrate 22. In fact, in some situations, it may be beneficial to use a concentrate 22 from one ore body and coarse ore substrates 20 from another. For example, one ore body may be easily concentrated or already have the characteristics desirable of a concentrate and another ore body may have a high concentration of carbonate minerals. In such a situation, it would be advantageous to use the first ore body to produce concentrate 22 and the second ore body to produce substrates 20. In this way, the ore from the second ore body can be neutralized in preparation for biooxidation while simultaneously improving the biooxidation results of the concentrate from the first ore body. Similarly, if an ore body contains a high concentration of metal sulfides that are difficult to float, improved flotation results can be achieved by first using the ore as coarse ore substrates 20 in the process according to the present invention.

Other preferred materials for substrates 20 include lava rock, gravel, and coarse rock containing carbonate minerals. These types of substrates will typically be used when the refractory sulfide ore body being mined is a waste heap or tailings pile, and, as a result, the ore has already gone through crushing and grinding.

An advantage of using lava rock is that it has a very rough, nonuniform surface morphology which increases the overall surface area of the substrates 20 for a particular particle size. Thus, for a given particle size, lava rock can be loaded with more concentrate than other substrates having a smoother surface.

Gravel, while typically having a fairly smooth surface, is an inexpensive substrate material. Coarse rock containing carbonate minerals is advantageous, because it will slowly release carbon dioxide as the acid from the biooxidation process neutralizes the carbonate minerals as explained above. This type of substrate would preferably be reused in the process only as long as it continues to release carbon dioxide during the biooxidation process.

Figure 3:
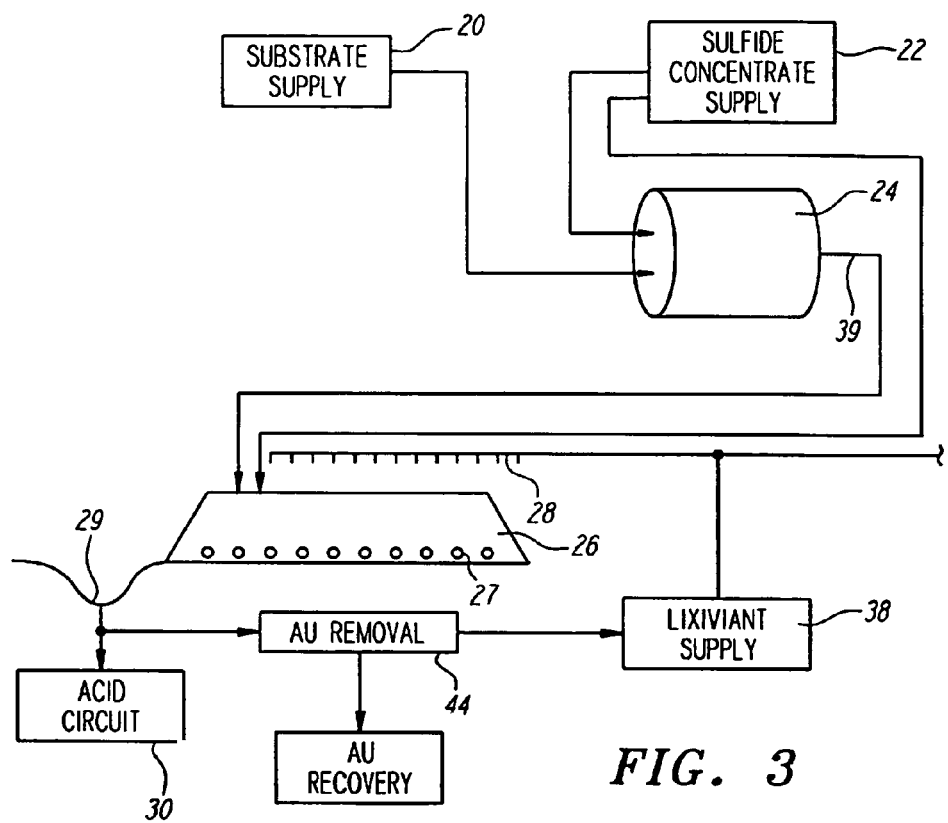
FIG. 3 is a schematic illustration of a process flow chart according to another embodiment of the present invention.

A third embodiment of the present invention is now described in connection with FIG. 3. The process according to the present embodiment is essentially a variation on the embodiment described in connection with FIG. 1. Accordingly, like items are referred to with the same reference numbers, and the description and considerations expressed with respect to these items in connection with FIG. 1 will be understood to apply equally to the present embodiment.

As with the second embodiment, the process according to the present embodiment can be used to liberate and recover precious metal values from a precious metal bearing refractory sulfide ore. For purposes of the present description, however, it is assumed that the sulfide mineral concentrate 22 is produced from a gold bearing refractory sulfide ore.

According to the present embodiment, a plurality of substrates 20 are coated with a sulfide mineral concentrate 22 in rotating drum 24 to produce a plurality of coated substrates 39. The plurality of coated substrates 39 are then stacked to form heap 26, which is used as a large nonstirred surface bioreactor.

The various considerations discussed above in connection with substrates 20, sulfide mineral concentrates 22, the formation of coated substrates 39, and the formation of heap 26 are all equally applicable here.

After heap 26 is formed the heap is inoculated with a biooxidizing bacteria to initiate the biooxidation process. As the biooxidation process proceeds, additional sulfide mineral concentrate 22 can be added to the top of heap 26. An advantage of adding additional sulfide mineral concentrate 22 to the top of heap 26 throughout the biooxidation process is that the amount of concentrate processed in the heap can be increased before tearing down and rebuilding. Furthermore, if coarse refractory sulfide ore is used for substrates 20, concentrate 22 will tend to biooxidize more quickly than the metal sulfide particles 40 found in the coarse ore. Thus, by adding additional concentrate 22 to the top of heap 26, the degree of biooxidation of the coarse ore substrates can be increased before heap tear down. In addition, by adding the sulfide mineral concentrate 22 to the top of heap 26, acid and ferric ions produced during its biooxidation will migrate to the lower part of the heap where bacterial growth may be inhibited due to toxins, which have not been washed from the ore early in the biooxidation process, or due to the lack of oxygen. As a result, biooxidation of the sulfide mineral concentrate and coarse ore substrates will proceed even if bacterial growth is not favored in this region.

There is another advantage to adding sulfide mineral concentrate 22 to the top of heap 26 after it has been undergoing biooxidation for some time, because such additions will increase the biooxidation rate in the heap. In the later stages of biooxidation of the coated substrates 39, most of the exposed and reactive sulfides will have already been oxidized, resulting in a slow down in the rate of biooxidation. This slow down in the rate of biooxidation can lead to a drop in iron levels and an increase in pH within heap 26. Addition of fresh reactive sulfide mineral concentrate 22 to the top of heap 26 can restart an active biooxidation process due to the high ferric levels produced from the biooxidation of the added concentrate, which in turn will increase indirect chemical leaching of the sulfide mineral concentrate 22 coated on substrates 20 and of metal sulfide particles imbedded in coarse ore substrates 20.

Fresh concentrate 22 can be added to the top of heap 26 until the flow channels within the heap begin to become plugged with the concentrate and biooxidized residue from the concentrate.

A second variation in the present embodiment from that in FIG. 1 is with respect to how the precious metal values are recovered from the heap following biooxidation. In the present embodiment, instead of tearing down the heap and then separating the biooxidized concentrate from the heap for gold extraction, gold is extracted from the biooxidized concentrate—and if a coarse ore substrate is used, from the substrates—by directly lixiviating the heap with a precious metal lixiviant. Preferably the lixiviant is one that functions at a low pH, such as thiourea, so the heap does not need to be neutralized prior to lixiviation. Furthermore, by using thiourea or other acid compatible lixiviant, the liberated gold values can be extracted from the heap on an intermittent basis. For example, heap 26 can be biooxidized for a period, liberated gold values extracted with an appropriate lixiviant, and then the biooxidation process resumed. A fresh concentrate 22 is preferably added to the top of heap 26 in slurry form with the resumption of the biooxidation process.

Gold is extracted from heap 26 by first allowing the bioleachate solution to drain from the heap to acid circuit 30 following a desired degree of biooxidation. After the heap is drained, an acid compatible lixiviant such as thiourea is pumped from the lixiviant supply 38 to the sprinkler system 28 where it is dispersed onto heap 26. As the lixiviant percolates through the heap, it dissolves liberated gold values from the sulfide mineral concentrate 22 and coarse ore substrates. The loaded lixiviant then collects at drain 29 where it diverted from the acid circuit to a gold removal process 44, which preferably comprises adsorbing the dissolved gold onto activated carbon or a synthetic resin. The barren lixiviant is then recycled to the lixiviant supply 38 and gold is recovered from the loaded activated carbon or synthetic resin. Processes for stripping adsorbed gold values from activated carbon and synthetic resin are well known in the art and need not be described herein.

Figure 4:
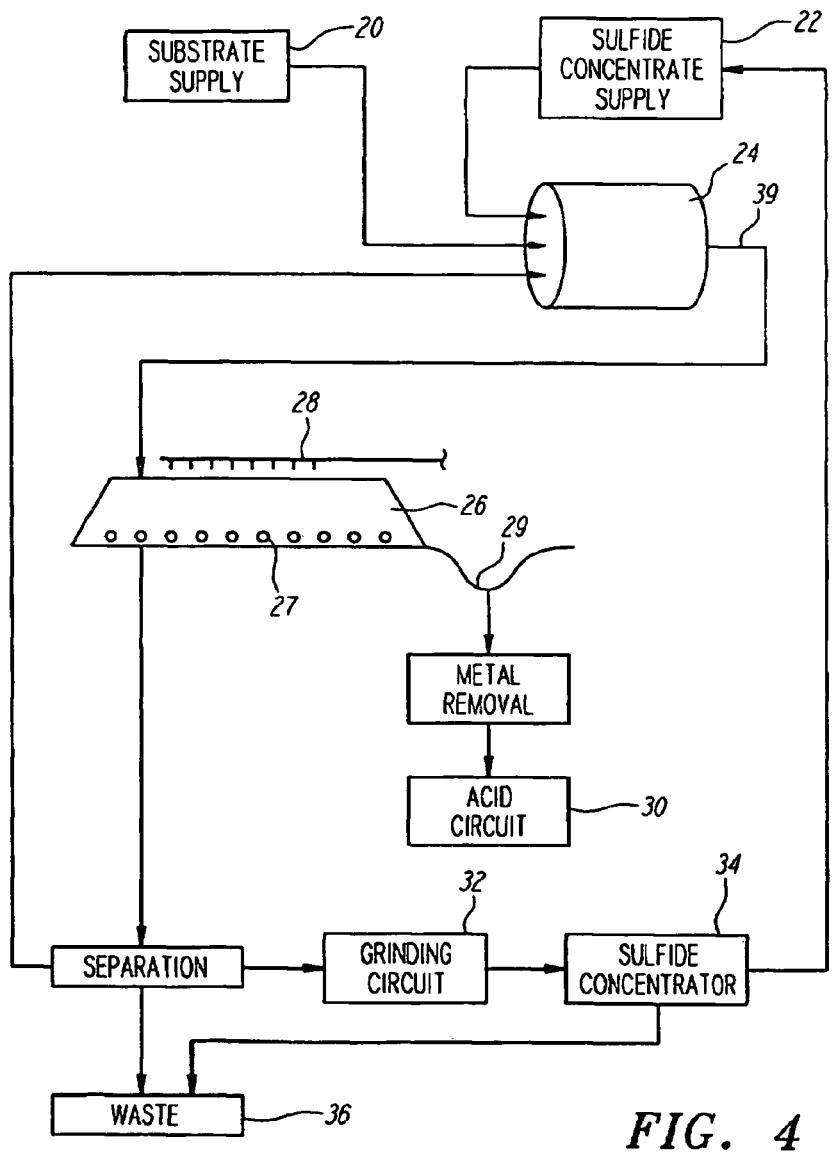
FIG. 4 is a schematic illustration of a process flow chart according to yet another embodiment of the present invention.

A process according to a fourth embodiment of the present invention is illustrated in FIG. 4.

FIG. 4 illustrates a process for liberating and recovering metal values from a sulfide ore. As the process according to the present embodiment has certain similarities to the embodiment described in connection with FIG. 1, like items have been referred to with the same reference numbers. Furthermore, the description and considerations expressed with respect to these items in connection with FIG. 1 will be understood to apply equally to the present embodiment.

According to the present embodiment, a sulfide mineral concentrate 22 is first produced from a sulfide ore. Concentrate 22 is comprised of a plurality of fine metal sulfide particles 40 and fine particles of sand or other gangue material 42.

Many different sulfide ores can be used to produce sulfide mineral concentrate 22. Foremost amongst the sulfide ores that can be treated in the present process are sulfide ores that contain sulfide minerals of base metals such as copper, zinc, nickel, iron, molybdenum, cobalt, or uranium. The metal values of interest in these ores are present in the metal moiety of the sulfide mineral particles in the ore. The metal values which are liberated and recovered, therefore, will depend on the specific sulfide minerals present in concentrate 22 produced from the ore. For example, if the sulfide ore used to produce concentrate 22 contains chalcocite, bornite, and/or chalcopyrite, then the metal values recovered will be that of copper. On the other hand, if concentrate 22 is a concentrate of sphalorite, the metal values recovered will be that of zinc.

After concentrate 22 is produced, sulfide mineral concentrate 22 is then coated on a plurality of substrates 20 to form coated substrates 39. This is accomplished as described in connection with FIG. 1 by adding a plurality of dry substrates 20 and a slurry of concentrate 22 to rotating drum 24, or, alternatively, by adding a plurality of dry substrates 20 and concentrate 22 to rotating drum 24 and then spraying the mixture with an aqueous solution. The plurality of coated substrates 39 produced in rotating drum 24 are stacked to form heap 26, which forms a large nonstirred surface bioreactor.

The various considerations discussed above in connection with substrates 20, sulfide mineral concentrates 22, the formation of coated substrates 39, and the formation of heap 26 are all equally applicable here.

After heap 26 is formed, the heap is inoculated with a biooxidizing bacteria to initiate the biooxidation process. As the metal sulfide particles 40 in concentrate 22 biooxidize, the metal moiety of the sulfide particles dissolves in the bioleachate solution as it percolates through the heap. After the bioleachate solution percolates through the heap, it is collected at drain 29. The bioleachate solution is then processed to recover one or more desired base metal values by removing them from the bioleachate solution using techniques well known in the art.

Following recovery of the desired metal values from the bioleachate solution, the solution can be processed in acid circuit 30 to remove any excess toxins as described in connection with FIG. 1 and then reapplied to the top of heap 26.

Once the biooxidation reaction has reached an economically defined end point, that is after the metal sulfide particles 40 on the surface of the coarse substrates 20 are biooxidized to a desired degree, the heap is broken down and the biooxidized concentrate separated from the coarse substrates 20. The biooxidized concentrate is then disposed of in waste or tailings pile 36. It is to be understood, however, that while the present embodiment has been described in terms of liberating and recovering base metal values from the metal moiety of the metal sulfide particles 40 in sulfide mineral concentrate 22, sulfide particles 40 can also include occluded precious metal values. After biooxidation of concentrate 22, therefore, any precious metal values that are liberated in concentrate 22 can be extracted and recovered as described in connection with FIG. 1 prior to the disposal of the biooxidized concentrate.

The coarse substrates 20 which have been separated from the biooxidized concentrate can be recycled to the rotating drum for a new coating of sulfide mineral concentrate 22. Alternatively, if coarse sulfide ore particles are used for substrates 20, they are preferably processed after one or more cycles through the process to form a sulfide mineral concentrate of any metal sulfide particles 40 which remain unoxidized in the coarse ore substrates. Sulfide mineral concentrate 22 is produced from the biooxidized coarse ore substrates as described in connection with the second embodiment.

Figure 5:
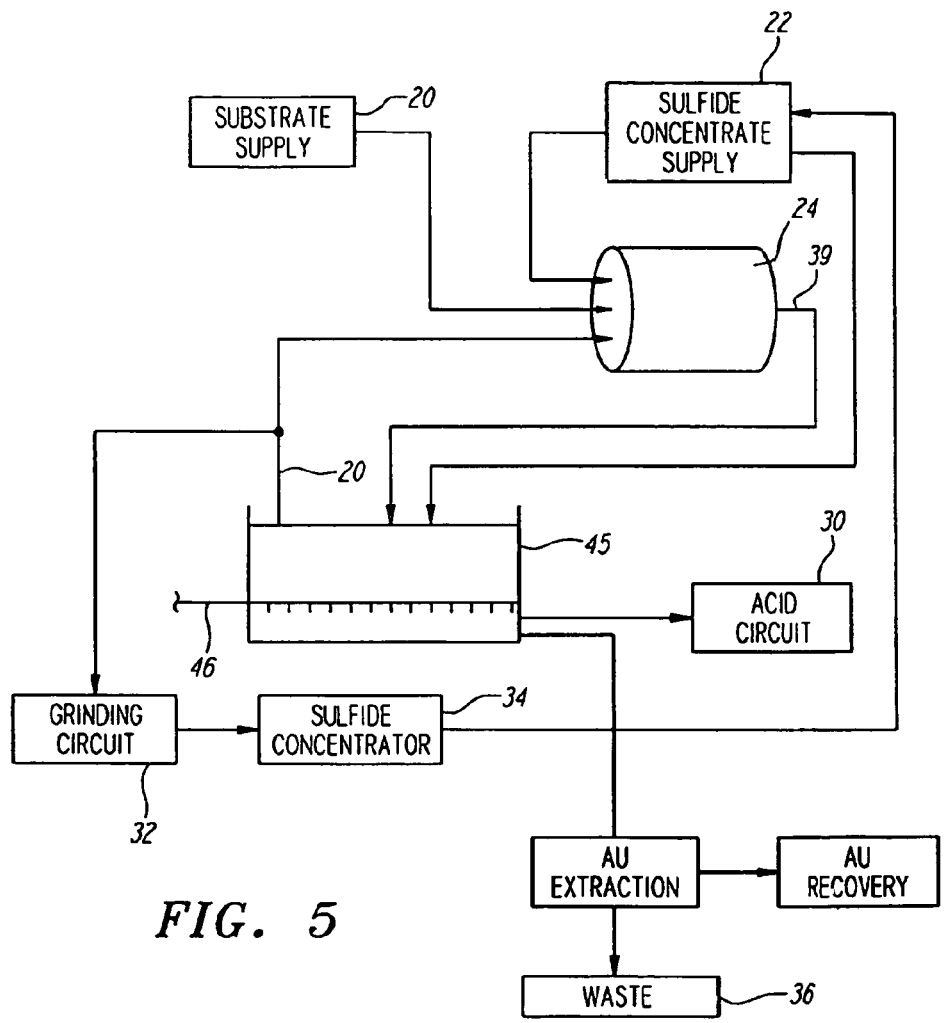
FIG. 5 is a schematic illustration of a process flow chart according to yet another embodiment of the present invention.

A process according to a fifth embodiment of the present invention is illustrated in FIG. 5. The process illustrated in FIG. 5 is for liberating and recovering precious metal values from precious metal bearing refractory sulfide ores using a nonstirred bioreactor. The process comprises producing a concentrate 22 of metal sulfide particles 40 from the refractory sulfide ore being processed. Concentrate 22 is then coated on a plurality of coarse substrates 20 to form coated substrates 39 using rotating drum 24 as described in connection with the second embodiment. After formation, coated substrates 39 are placed in a tank 45 for biooxidation. By biooxidizing substrates 39 in tank 45, a large nonstirred surface bioreactor is created which has a very large surface area. Thus, tank 45 takes the place of heap 26 in the process according to the second embodiment. Accordingly, the various considerations discussed above in the second embodiment with respect to substrates 20, sulfide mineral concentrates 22, the formation of coated substrates 39, and the formation of heap 26 are all equally applicable to the biooxidation of coated substrates 39 in tank 45 in the present embodiment.

During the biooxidation of concentrate 22 on coated substrates 39, bioleachant maintenance solutions are added to the tank from the top using any of a number of well known techniques. The bioleachate solution that percolates through the tank is drained from the tank and processed in acid circuit 30 as described in connection with FIG. 1 prior to reuse in the process.

Air can be blown into the tank during the biooxidation process to improve the oxygen levels in the bioreactor and to improve heat dissipation. Air is preferably blown into tank 45 through a series of perforated pipes 46 which are connected to a blower (not shown).

If desired, additional concentrate 22 can be added to the top of the coated substrates 39 in tank 45 throughout the biooxidation process. As described above in connection with the third embodiment, by adding additional concentrate to the bioreactor during the biooxidation process, the rate of biooxidation within the bioreactor can be maintained at a high level throughout the biooxidation process.

An advantage of using tank 45 over heap 26 for the bioreactor is that it makes separation of the biooxidized concentrate 22 from the substrates 20 easier. After the concentrate 22 is biooxidized to a desired end point, separation of the biooxidized concentrate from the substrates is accomplished by filling the tank with water, and then rapidly draining the tank. The biooxidized concentrate will be carried with the draining water. This process can be repeated several times to improve separation results. Tank 45 is also preferably equipped with a screen in the bottom of the tank which has a mesh size that is less than the size of the substrates, but larger than the concentrate particle size to aid the separation process.

After separation, the biooxidized concentrate is leached with a precious metal lixiviant to extract the liberated gold or other precious metal values. The dissolved gold values are then recovered from the lixiviant by contacting the solution with activated carbon or a synthetic resin. Preferably the lixiviation is carried out in the presence of the activated carbon or a synthetic resin so that the dissolved gold values are immediately removed from the solution as they are dissolved. The gold adsorbed on the activated carbon or synthetic resins can be recovered using techniques well known in the art.

Once the precious metal values have been extracted from the biooxidized concentrate, the concentrate can be disposed of in waste or tailings pile 36.

As in the second embodiment, the coarse substrates 20 that have been separated from the biooxidized concentrates can be recycled to the rotating drum for a new coating of sulfide mineral concentrate 22. Substrates 20 can be reused as long as they retain their mechanical integrity. If coarse refractory sulfide ore particles are used as substrates 20, they are preferably processed at some point, preferably after one to three cycles, to recover liberated gold values. This is accomplished in the same manner as described in connection with the second embodiment.

The preferred embodiments of the invention having been described, various aspects of the invention are further amplified in the examples that follow. Such amplifications are intended to illustrate the invention disclosed herein, and not to limit the invention to the examples set forth.

EXAMPLE 1

A sample of low grade (3.4 ppm) gold ore, which was known to be refractory to leaching with cyanide due to sulfides, was crushed. The ore was then separated into a −0.62 cm fraction (47.4 wt %) and a −0.31 cm fraction (remainder). The −0.31 cm fraction was then further ground to 95% passing a 75 μm sieve to aid in producing a refractory pyrite concentrate by flotation.

Water was added to the ground sample until it reached a 30% pulp density. The ore pulp was then adjusted to a pH of 10 and treated with $Na_2SiO_3$ at 6 Kg/tonne of ore for 12 hours to remove the clay material. The clay material was removed as the fraction that did not settle after 12 hours.

Because clays can cause problems with flotation, a step that permits the non clay material to settle out was added to remove the clay fraction before floating the sample.

The clay fraction was under 3% of the total ore weight, yet it contained almost 5% of the gold in the ore. The removal and subsequent flotation of the clay fraction produced a very small weight fraction (0.1% of the total ore weight), but it contained over 17 ppm gold. Cyanide leaching of the clay flotation tail extracted over 76% of the gold contained therein. The total amount of gold contained in the clay flotation tail was 1.08 ppm.

Before floating, the main fraction of ground ore (+5 μm to −75 μm) was conditioned with $CaSO_4$ at 2.0 Kg/tonne for ten minutes by mixing in a Wemco flotation cell. This was followed by 10 minutes of mixing with Xanthate at 100 g/tonne which was then followed by 5 minutes of mixing with Dowfroth D-200 at 50 g/tonne. The sample was then floated for 20 minutes at a pulp density of 30%. Four Kg of the main fraction was processed in 8 separate batches of 500 g each. The sulfide concentrates obtained from these flotations were collected and combined and refloated in a column.

Three fractions were collected, the tail from the Wemco float, the tail from the column float, and the sulfide concentrate, each of these fractions were dried and weighed. The tail from the Wemco float was 35.4 wt % of total ore weight and contained 1.88 ppm of gold. Cyanide leaching of this fraction yielded 67% of its gold. This was higher than the recovery for cyanide leaching of the whole ore, which was 63%. The column tail contained 3.56 ppm of gold. The gold recovery from this fraction by cyanide leaching was 76.6%.

The sulfide concentrate weighed 753 g which represented 8.8% of the total ore (+0.31 cm and −0.31 cm fractions). Analysis of a small fraction of the concentrate indicated it contained 6.5 ppm of gold. This fraction was coated on to the 47.4 weight percent of the +0.31 cm ore. The dry pyrite concentrate was spread over the surface of the coarse ore by rolling in a drum rotating at 30 rpm while spraying a mixture of 2,000 ppm ferric ion and 1% Nalco #7534, which is an agglomeration aid. The pH of the solution was 1.8.

The mixture of concentrate on coarse ore support was placed into a 3 inch column. Air and liquid were introduced from the top. The column was inoculated with 10 ml of *Thiobacillus ferrooxidans* bacteria at an O.D. of 2.6 or about $1.1 \times 10^{10}$ bacteria per ml.

The bacteria were grown in an acidic nutrient solution containing 5 g/l ammonium sulfate and 0.83 g/l magnesium sulfate heptahydrate. The pH of the solution was maintained in the range of 1.7 to 1.9 by adjustment with sulfuric acid ($H_2SO_4$). The solution also contained iron at 20 g/liter in the form of ferric and ferrous sulfate.

The bacteria were added to the top of the column after the pH was adjusted to a pH of 1.8. The liquid, introduced to the top of the column throughout the experiment, was pH 1.8; with 0.2×9 K salts and 2,000 ppm ferric. The extent of iron oxidation was determined by analysis of the solution eluting off the column minus the iron introduced by the 2,000 ppm ferric feed.

The composition of the standard 9 K salts medium for *T. ferrooxidans* is listed below. The concentrations are provided in grams/liter.

| | |
|---|---|
| $(NH_4)SO_4$ | 5 |
| KCl | 0.17 |
| $K_2HPO_4$ | 0.083 |
| $MgSO_4 \cdot 7H_2O$ | 0.833 |
| $Ca(NO_3) \cdot 4H_2O$ | 0.024 |

The notation 0.2×9 K salts indicates that the 9 K salt solution strength was at twenty percent that of the standard 9 K salt medium.

After 60 days the amount of iron leached off of the column indicated that about 50% of the pyrite had been biooxidized. The experiment was stopped and the mixture separated into a +600 μm fraction and a −600 μm fraction. Each fraction was ground to 95% minus 75 μm and then leached with a 500 ppm cyanide solution in a 96-hour bottle roll analysis. Activated carbon was added to the bottle roll test to absorb any dissolved gold.

The gold recovery of the −30 mesh fraction was 83.7%. The −30 mesh material had an increased head gold value of 8.87 ppm due to loss of pyrite weight. The coarse +30 mesh fraction, on the other hand, had a gold recovery of 57% and a head gold value of 2.24 ppm. This indicated that the concentrate pyrite that was coated on the outside of the coarse rock had biooxidized faster than the coarse fraction of the rock.

EXAMPLE 2

Another comparative test was made. In this example, the biooxidation rates of ore size fractions were compared. The ore, which was provided by the Ramrod Gold Corporation, was crushed to 1.9 cm. The −0.31 cm ore fraction was removed and used to form a concentrate. The ore sample had less than 0.08 oz. of gold per ton of ore (2.7 ppm). The sample contained both arsenopyrite and pyrite. The concentrate was made by ball milling 5 Kg of the −0.31 cm inch ore until it passed −75 μm, the ball milled ore was then floated with Xanthate to form a pyrite concentrate. Before flotation clay was removed by settling with $Na_2SiO_3$ at 6 Kg/tonne of ore for 8 hours or more. The flotation was done in small batches of 500 g each in a laboratory Wemco flotation cell. Potassium Amyl Xanthate was used as a collector at a concentration of 100 g/tonne along with sodium sulfide at 1.5 Kg/tonne and Dowfroth D-200 at 50 g/tonne. The pyrite concentrate constituted 4.5% of the weight of the −0.31 cm ore fraction. However, this ore fraction contained over 80% of the gold and pyrite for the milled ore. The concentrate contained approximately 17.4% iron, 15.7% sulfur and approximately 40 ppm gold. The +0.31 cm ore contained 0.9% iron and 0.18% sulfur.

A sample of 140 g of this concentrate was coated onto 560 g of +0.31 cm coarse ore. The concentrate was added as a dry powder to the coarse ore. The mixture was then rotated in a small plastic drum at 30 rpm to spread the dry concentrate over the rock support. Liquid which contained 2,000 ppm ferric ion and 1% Nalco #7534 was sprayed onto the mixture until all the concentrate was coated onto the rock. The pH of the liquid was maintained at 1.8. The amount of liquid used was estimated to be between 5 and 10 percent of the weight of the coarse ore and concentrate. The 700 g mixture of concentrate on coarse ore substrates was placed into a 3 inch column. The height of the ore after being placed in the column was approximately 5 inches. Air and liquid were introduced from the top of the column. The column of concentrate coated on coarse ore substrates was inoculated with about 10 ml of bacteria at an O.D. of 2.0 or about $8 \times 10^9$ bacteria per ml.

The bacteria were a mixed culture of *Thiobacillus ferrooxidans*, which were originally started with ATCC strains #19859 and 33020. The bacteria were grown in an acidic nutrient solution containing 5 g/l ammonium sulfate and 0.83 g/l magnesium sulfate heptahydrate. The pH of the solution was maintained in the range of 1.7 to 1.9 by adjustment with sulfuric acid ($H_2SO_4$). The solution also contained iron at 20 g/liter in the form of ferric and ferrous sulfate.

The bacteria were added to the top of the column after the pH was adjusted to pH 1.8. The liquid, introduced to the top of the column throughout the experiment had a pH of 1.8 with 0.2×9 K salts and 2,000 ppm ferric ion. The extent of iron oxidation was determined by analysis of the solution eluting off the column minus the iron introduced by the 2,000 ppm ferric feed.

Figure 6:
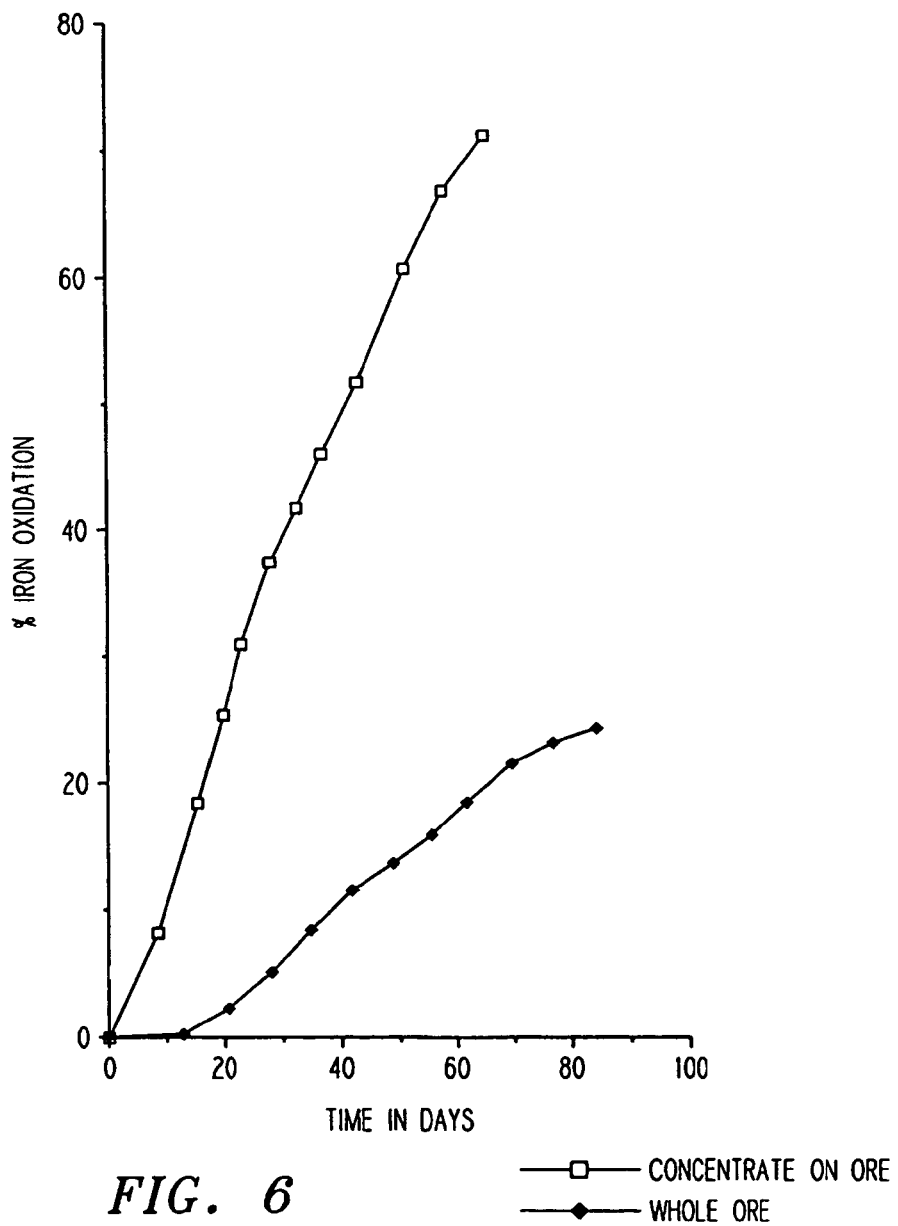
FIG. 6 is a graph illustrating the percent of iron oxidation versus time for a whole ore compared to a process according to the present invention.
Figure 7:
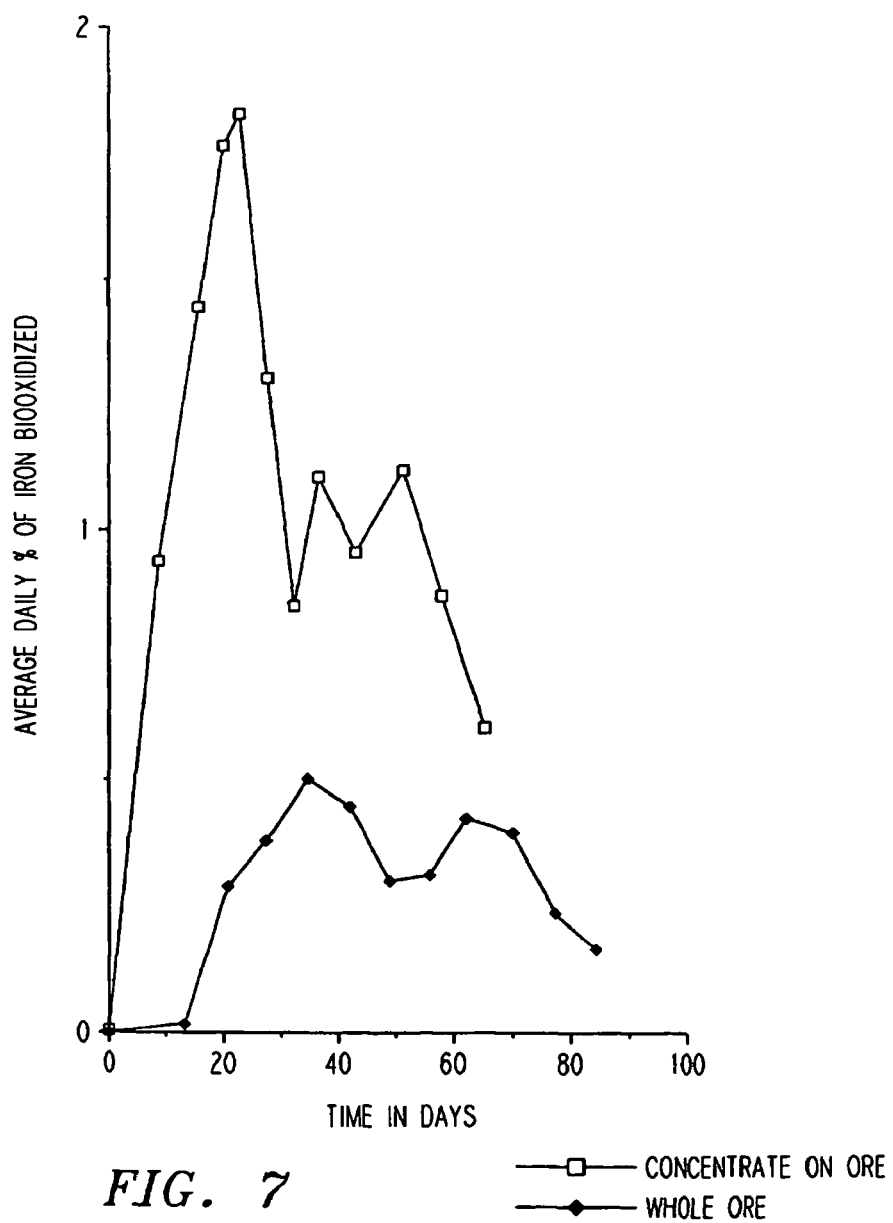
FIG. 7 is a graph comparing the average daily biooxidation rate of a whole ore against that of a process according to the present invention.

This ore was low in sulfides having a concentration of less than 1% of its weight. By making a concentrate on the coarse rock at 20% by weight, the concentration of both the pyrite and gold could be increased by over tenfold. This increased the rate of biooxidation as seen in FIGS. 6 and 7 over that for the whole ore. Not only did this process expose more of the pyrite to air and water but it also increased the amount of ferric ion and acid generated per unit volume of ore in the column model for a heap.

FIG. 6 shows the amount of oxidation as determined by percent iron leached for both the pyrite concentrate of this ore on +0.31 cm coarse ore and the whole ore itself. As the graph shows the concentrate process was biooxidized to about 40% in the first 30 days and over 65% in the first 60 days. Whereas the whole ore was only biooxidized to 24% in 84 days. The average daily biooxidation rates are shown in FIG. 7. The highest average daily rate of the coated concentrate was 1.8% per day compared to an average daily rate of only 0.5% for the whole ore. As FIG. 7 illustrates, the coated concentrate sample did not take as long to begin biooxidizing the sample. This means that the coated concentrate process is more likely to achieve complete biooxidation in a reasonably short time.

Table 1 below shows the specific data points graphed in FIGS. 6 and 7 for the concentrate on coarse ore process and for the whole ore process which was done for comparison.

After 68 days the concentrate coated on coarse ore column was taken down. The biooxidized material was separated into a plus 180 μm fraction and a minus 180 μm fraction. The weight of the fine material had increased from 140 g to 150 g. The total amount of iron removed from the system during the 68 days of biooxidation was 21.5 g which represents 46 g of pyrite. The weight of the coarse rock decreased by 54 g. This was believed to be due to breakdown of the rock to finer material due to the biooxidation process. The total weight after biooxidation was 656 g which was 44 g less than the starting material. This fit well with the estimated 46 g of pyrite oxidized.

TABLE 1

| | Concentrate Process | | | Whole Ore Process | |
|---|---|---|---|---|---|
| # of Days | % Fe leached | % Fe/day | # of days | % Fe Leached | % Fe/day |
| 0 | 0.0 | 0.00 | 0 | 0.0 | 0.00 |
| 9 | 8.4 | 0.93 | 13 | 0.2 | 0.01 |
| 16 | 18.5 | 1.44 | 21 | 2.5 | 0.29 |
| 20 | 25.5 | 1.76 | 28 | 5.1 | 0.38 |
| 23 | 31.0 | 1.82 | 35 | 8.6 | 0.50 |
| 28 | 37.5 | 1.30 | 42 | 11.7 | 0.44 |
| 33 | 41.7 | 0.84 | 49 | 13.8 | 0.29 |
| 37 | 46.1 | 1.10 | 56 | 15.9 | 0.31 |
| 43 | 51.8 | 0.95 | 62 | 18.4 | 0.42 |
| 51 | 60.7 | 1.11 | 70 | 21.5 | 0.39 |
| 58 | 66.7 | 0.86 | 77 | 23.1 | 0.23 |
| 65 | 70.9 | 0.60 | 84 | 24.3 | 0.16 |

Two samples of the −180 μm material and one sample of the +180 μm material were leached with cyanide. To leach the samples, bottle rolls were done for 96 hours, the leachant was maintained at 500 ppm cyanide. The +180 μm coarse ore support rock was ground to 95%—75 μm before doing the bottle roll. All bottle rolls were done with activated carbon in the leach solution.

Sulfide analysis of the minus 180 μm fraction after 68 days of biooxidation showed the sample still contained 8.8% sulfides which was 56% of the starting level. This was a lower percent oxidation than indicated by the iron leached off during the column experiment. The gold recovery increased to 84.3% for the high grade (38 ppm) −180 μm fraction and 79.5% for the +180 μm low grade (3 ppm) fraction. This is a substantial increase from the 45.6% recovery of the unoxidized ore.

EXAMPLE 3

A sample of 70% minus 75 μm gold ore from a mine in the Dominican Republic was used to make a sulfide float concentrate. The ore sample was obtained from the tailing pile at the mine that had already been leached with cyanide. The ore sample still contained gold values of over 2 g per tonne which were occluded within the sulfides and not directly leachable by cyanide.

To form the sulfide concentrate, several kilograms of this sample were further ground to 95% minus 75 μm. The ground sample was then floated to form the sulfide concentrate. The flotation was done in small batches of 500 g each in a laboratory Wemco flotation cell. Before flotation, the ground ore sample was adjusted to a pulp density of 30%. The ore slurry was then mixed with 1.5 Kg/tonne sodium sulfide ($Na_2S$) for 5 minutes at pH 8.5. Then potassium amyl Xanthate was added as a collector at 100 g/tonne and mixed for 5 minutes. Next 50 g/tonne of Dowfroth D-200 was added and mixed for 5 minutes. Finally, air was introduced to produce a sulfide concentrate that contained 17.4% iron and 19.4% sulfide by weight and 14 g of gold per tonne of concentrate. A plurality of coated substrates were then made by coating 140 g of the sulfide concentrate onto 560 g of +0.31 cm −0.62 cm granite rock. The concentrate was added as a dry powder to the granite rock. The mixture was then rotated in a small plastic drum at 30 rpm to spread the dry pyrite over the support material. A liquid which contained 2,000 ppm ferric ion and 1% Nalco #7534 agglomeration aid was sprayed on the mixture until all the sulfide concentrate was coated onto the wetted granite rock. The solution was maintained at a pH of 1.8.

The coarse rock in this case had no iron or gold value. The rock, however, contained a small amount of mineral carbonate which tended to keep the pH high at first but also provided $CO_2$ as a carbon source for the bacteria.

The 700 g of concentrate coated rock was put into a column. A 0.2×9 K salts and 2,000 ppm ferric ion solution having a pH of 1.6 was introduced through the top of the column at a flow rate of about 300 ml/day. Then the column was inoculated with 10 ml of bacteria as in Example 2. After the pH of the concentrate coated rock substrate was adjusted to a pH of 1.8, the pH of the influent was set at 1.8. Air was also introduced through the top of the column.

Figure 8:
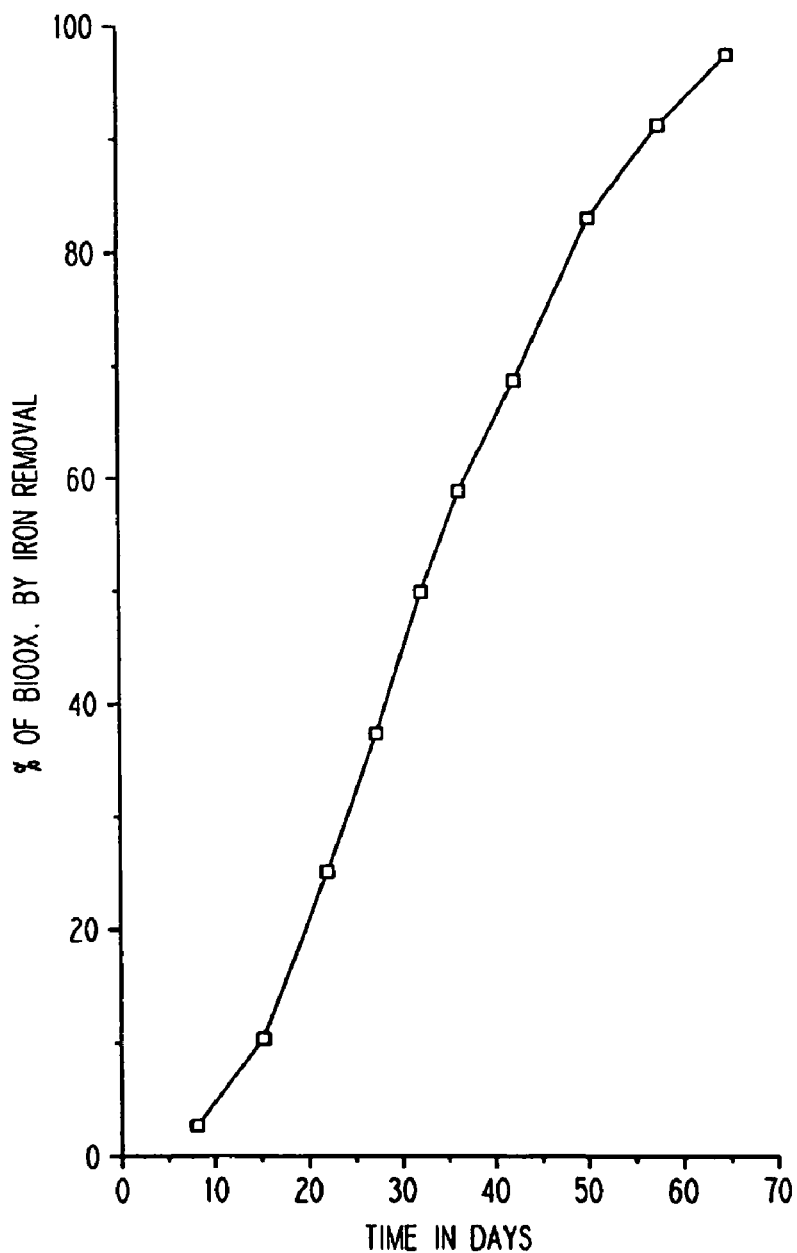
FIG. 8 is a graph illustrating the percentage of biooxidation for another process according to the present invention.
Figure 9:
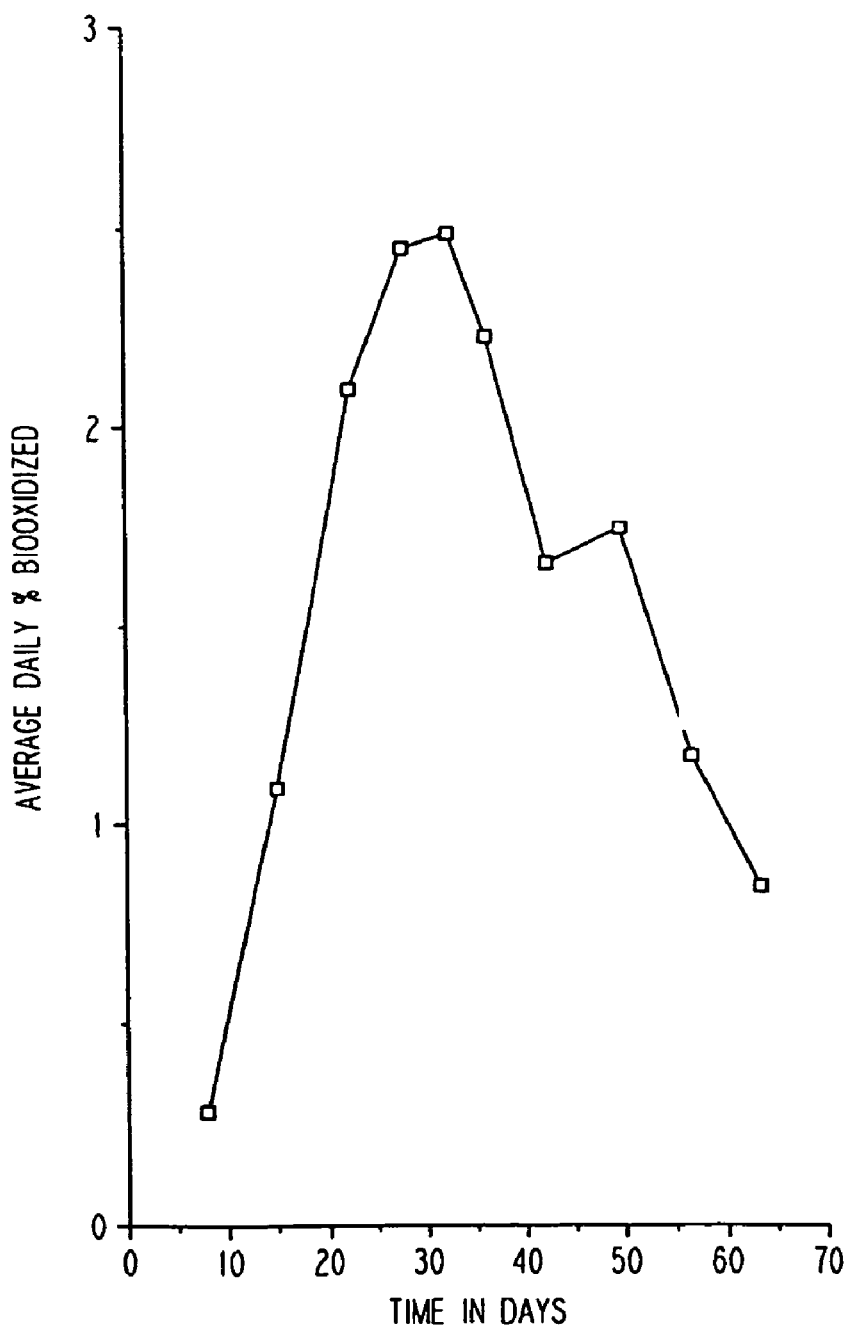
FIG. 9 is a graph illustrating the average daily rate of biooxidation for the process corresponding to FIG. 8.

FIG. 8 graphically illustrates the percent of biooxidation as determined by the percent of iron leached from the concentrate. The average daily percentage of biooxidation was calculated and is listed in Table 2 and is graphically illustrated in FIG. 9. The percentage biooxidation was determined by dividing the total iron removed by the total iron contained within the concentrate. The rate of biooxidation was slow to start as the pH was adjusted and the bacteria built up and adapted. However, after about two weeks the rate increased rapidly and reached a maximum after 30 days. By this time almost 50% of the total iron had been biooxidized. The process continued with a gradual slowdown as the remaining pyrite was consumed. At the end of 64 days nearly 97% of the iron had been biooxidized. Even with the concentrate almost completely biooxidized and the rate slowing down near the end of the process, the average daily rate was still near 1%/day. After 70 days the biooxidation was stopped. The biooxidized concentrate was separated into a plus 180 μm fraction and a minus 180 μm fraction. The weight of the biooxidized concentrate had decreased from 140 g to 115 g. The total amount of iron removed from the system during the 70 days of biooxidation was 25.9 g which represents 55.5 g of pyrite. The weight of the granite rock decreased by 98.8 g. This was believed to be due to a breakdown of the calcium carbonate in the rock by the acid as well as the breakdown of the rock to finer material. The total weight decreased by 123.3 g which was 67.8 g more than predicted by biooxidation of pyrite alone.

TABLE 2

| Time in Days | % Bioox. | % Bioox./Day |
|---|---|---|
| 5 | 2.590 | 0.288 |
| 15 | 10.270 | 1.100 |
| 22 | 24.970 | 2.100 |
| 27 | 37.250 | 2.450 |
| 32 | 49.700 | 2.490 |
| 36 | 58.610 | 2.230 |
| 42 | 68.580 | 1.660 |
| 50 | 82.580 | 1.750 |
| 57 | 90.870 | 1.180 |
| 64 | 96.820 | 0.850 |

The sample of −180 μm material was leached with 500 ppm cyanide in a bottle roll for 96 hours. The +180 μm granite rock was also leached with 500 ppm cyanide to determine how much gold could be stuck to the support rock in a process that used barren rock as a supporting substrate. Analysis of the −180 μm material showed it still contained 9.7% sulfide which indicated only about 50% oxidation.

Gold extraction was 77% from the −180 μm fraction. This gold was recovered from gold ore that had already been leached with cyanide, thus demonstrating that the process according to the present invention is even applicable to ores which heretofore have been considered waste. And while any recovery would be an improvement over the process currently practiced at the mine, the process according to the present invention was able to recover 77% of the gold in what was previously considered tailings.

Cyanide leaching of the granite support rock showed that it had picked up 0.15 ppm of gold which was 3.4% of the total gold.

EXAMPLE 4

A sample of gold bearing refractory sulfide ore that had been crushed to 80% passing 0.62 cm was prepared for testing as support rock. The ore was from the Western States mine located in Nevada, and contained a high concentration of carbonate minerals in the form of limestone. The fine material (less than 0.31 cm) was removed in order to allow for good air flow. A four kilogram sample of the +0.31 cm to −0.62 cm rock was coated with one kilogram of a gold bearing pyrite concentrate provided by another mining company. The coating was formed by placing a the coarse ore substrates and dry concentrate into a small rotating drum and spraying the mixture with a liquid which contained 2,000 ppm ferric ion and 1% Nalco #7534 agglomeration aid until all the sulfide concentrate was coated onto the wetted granite rock.

Iron analysis of both samples showed that the concentrate contained 210 grams of iron and the four kilograms of support rock contained 42.8 grams of iron.

Figure 10:
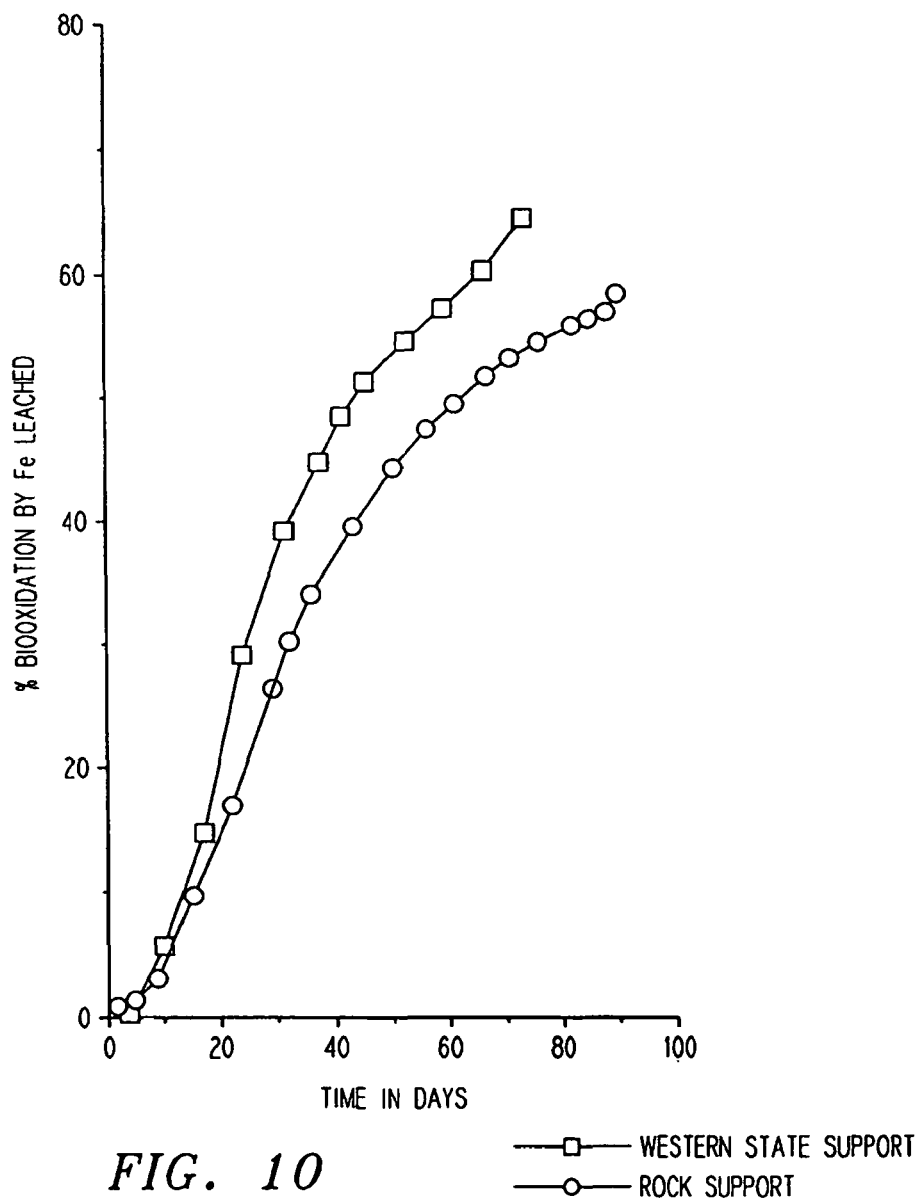
FIG. 10 is a graph illustrating the percentage of biooxidation as a function of time for a pyrite concentrate coated on a barren rock support and the same pyrite concentrate coated on a refractory sulfide ore support that contains a high concentration of mineral carbonate.

The five kilograms of coated ore substrates was placed in a 3 inch column. To start the biooxidation process, a solution having a pH of 1.3 and containing 2,000 ppm of ferric ions was passed through the column at about one liter per day. After seven days, the pH of solution leaving the column was below pH 2.5. At this point the column was inoculated with 10 ml of a culture of *Thiobacillus ferrooxidans* bacteria (as in Example 2) and the pH of the feed solution was raised to a pH of 1.8. After a total of fifteen days the column was generating acid at a pH of 1.7 and an Eh of 700 mV. The progress of the biooxidation process was followed by measuring the iron leaching off the column of concentrate coated nominal 0.62 cm ore. This data was compared with the data from an experiment using the same concentrate coated on a sample of barren rock. The rates of the leaching in both cases are compared in graph form in FIG. 10. The fact that the Western States experiment was slightly faster suggests that the coarse ore support rock was also oxidizing to some extent.

The Western States column experiment ran for a total of 74 days and leached a total of 166 grams of iron out of the system or 66% of the total iron in both the concentrate and support rock. Most of the iron was leached from the concentrate, but some came from the support rock. The weight of the concentrate changed from 1,000 grams to 705.8 grams after biooxidation. The four kilograms of Western States coarse ore support rock decreased to 3695.5 grams, which corresponds to a loss of 304.5 grams or 7.6% of its weight after biooxidation. The decrease in weight of the coarse ore support rock was due to a combination of biooxidation of its pyrite, acid leaching of the carbonate in the ore, and physical abrasion of the ore.

The 705.8 grams of biooxidized concentrate, which was originally from another mine in Nevada, was tested for gold extraction using a cyanide bottle roll test. The gold recovery before biooxidation was 46%. After biooxidation it increased to 86%. This same gold recovery was achieved by biooxidizing the concentrate to the same extent on the gravel support material.

The acid consumption of the Western States ore was measured before and after its use as a support rock for biooxidation. The amount of sulfuric acid required to adjust the pH down to 2 before biooxidation was 31.4 g per 100 g ore. The amount of acid required to adjust the pH down to 2 after biooxidation was 11 g per 100 g ore. This would mean that about 20% of the weight of the support rock was acid neutralized during the 74 days of biooxidation. This was larger than the 7.6% loss in weight of the support rock. This may be due to a precipitate forming on the rock after biooxidation or sample to sample variation in the percent limestone.

Several conclusions can be drawn from this test. First, a low pH biooxidation process can occur on the surface of a high carbonate ore. Second, with the +0.31 cm to −0.62 cm support material, the process of neutralization by the pH 1.8 acid was slow enough that the carbonate in the ore was still not completely removed after 74 days. The process of slow acid neutralization is beneficial to the bacteria, because the neutralization of the limestone in the ore will provide needed $CO_2$ for the biooxidizing bacteria's carbon source. Third, the coarse ore support was benefited from the process because smaller nonfloatable sulfides in the Western State ore were biooxidized.

Based on the amount of neutralization that occurred in about 2 months of the +0.31 cm to −0.62 cm coarse ore support, a +0.62 cm to −1.9 cm coarse ore support rock would be best for a full scale process. With the larger coarse ore support, it will take 90 to 120 days in a heap biooxidation process to make the best use of the limestone neutralization and to biooxidize the smaller floatable sulfides in the coarse ore support rock. The time it takes to biooxidize the coating of sulfide spread on the outside of the coarse ore support is generally less than 90 days. Therefore, the coarse ore support may be used several times before it is ground up and floated to make a pyrite concentrate for biooxidation on the surface of a coarse ore support rock.

Prior to biooxidation, two attempts were made to produce a concentrate by flotation of the Western States ore. One method used only xanthate and produced only a small recovery of gold (less than 12%) into the pyrite concentrate. The tail from this flotation still contained 4.0 g Au/tonne. Extraction of the flotation tail with cyanide only recovered 17% of the gold remaining in the tail.

A second attempt at flotation used both kerosene to float off a carbon concentrate followed by xanthate to produce a pyrite concentrate. The combined weight of these concentrates accounted for 18 weight % of the ore, which was double the 7.4 weight % concentrate produced using only xanthate. The combined gold recovery for both concentrates increased to 53.8% of the gold. The tail from this flotation decreased to 2.12 g/tonne in gold. Extraction of the tail with cyanide recovered only 34.5% of the gold remaining in the tail after flotation of both concentrates.

The third attempt at flotation was done with the Western States ore after it had been used as a support rock for biooxidation in the present example. The +0.31 cm to −0.62 cm ore substrates were ground to −75 μm and then floated using xanthate as a collector. This formed a pyrite concentrate of 33.4 g Au/tonne and 7.9% of the original ore weight. The tail from this flotation contained 1.09 g Au/tonne. The recovery of the gold into the pyrite concentrate was 72.4%. Cyanide extraction of the 1.09 g/tonne tail recovered 48.7% of the gold to produce a final tail of 0.56 g/tonne.

The 33.4 g Au/tonne pyrite concentrate was biooxidized in a shake flask experiment. After biooxidation the cyanide extraction had increased to 99% gold recovery. This result showed that this concentrate was gold containing pyrite that could be biooxidized along with other concentrate in the coated substrate process.

As can be seen from the flotation results contained in Table 3 below, by floating the Western States ore after it was used as a support material for biooxidation, a high grade pyrite concentrate was more easily produced, and the flotation tail was less refractory to cyanide extraction. This may have been due to a chemical change to the pyrite during the 74 days in the high ferric and low pH conditions of biooxidation. Alternatively, the nonfloating sulfides may have been made less refractory by a combination of ferric and bacterial oxidation

TABLE 3

FLOTATION RESULTS

|  | 1st Pyrite Float | 2nd float | 3rd after bioox. float |
|---|---|---|---|
| grinding | −75 μm | −75 μm | −75 μm |
| reagents for flotation | Xanthate Dowfroth | Kerosene NaSiO3 Xanthate Dowfroth | NaS, CuSO4 Xanthate Dowfroth |
| Wt. % of pyrite conc. | 7.4% | 3.2% | 7.9% |
| Wt. % of carbon conc. | — | 14.8% | — |
| Total wt. % of conc. | 7.4% | 18.0% | 7.9% |
| Grade of conc. | 6.4 g/t | 26.4 g/t | 33.4 g/t |
| % gold in conc. | 11.3% | 53.8% | 72.4% |
| Gold in tail before CN | 4.0 g/t | 2.12 g/t | 1.09 g/t |
| Gold in tail after CN | 3.32 g/t | 1.39 g/t | 0.56 g/t |
| Gold recovery from leaching tail by CN | 17.2% | 34.5% | 48.7% |
| Combined total recovery | 26.4% | 69.2% | 85.4% |
| Head grade of sample tested | 4.18 g/t | 3.77 g/t | 3.64 g/t |

Although the invention has been described with reference to preferred embodiments and specific examples, it will readily be appreciated by those of ordinary skill in the art that many modifications and adaptations of the invention are possible without departure from the spirit and scope of the invention as claimed hereinafter. For example, while the processes according to the present invention have been described in terms of recovering gold from refractory sulfide or refractory carbonaceous sulfide ores, the processes are equally applicable to other precious metals found in these ores such as silver and platinum. Similarly, the process according to the present invention may, as one skilled in the art would readily recognize, be used to biooxidize sulfide concentrates from metal sulfide ores such as chalcopyrite and sphalorite.

What is claimed:
1. A method of biotreating a solid material comprising an organic compound, said method comprising:
   a. forming a nonstirred bioreactor having a void volume of greater than or equal to 25% with a mixture including a solid material to be biotreated and a plurality of coarse substrates having a particle size greater than or equal to about 0.6 cm, the solid material to be biotreated comprising an organic material, and the mixture including sufficient coarse substrates to provide the reactor with at least 100 square meters of surface area per cubic meter of reactor space; and b. biotreating the solid material in the bioreactor until the organic material within the bioreactor is reduced to a desired concentration.

2. The method of claim 1, wherein the solid material is soil.

3. The method of claim 1, wherein the organic material is at least one organic material selected from the group consisting of waste oil, grease, jet fuel, diesel fuel, crude oil, benzene, toluene, ethylbenzene, xylene, polyaromatic hydrocarbons (PAH), polynuclear aromatics (PNAs), pentachlorophenol (PCP), polychlorinated biphenyls (PCBs), creosote, pesticides, 2,4,6-trinitrotoluene (TNT), hexahydro-1,3,5-trinitro-1,3,5-triazine (RDX), octahydro-1,3,5,7-tetranitro-1,3,5,7-tetrazocine (HMX), N-methyl-N-2,4,6-tetranitroaniline, and nitrocellulose (NC).

4. The method of claim 1, wherein the organic material includes cellulose.

5. The method of claim 1, wherein the void volume is greater than or equal to about 35%.

6. The method of claim 1, wherein said coarse substrates have a nominal particle size that is greater than about 0.6 cm and less than about 2.54 cm.

7. The method of claim 1, further comprising the step of forming the mixture by combining the solid material to be biotreated with the coarse substrates in a rotating drum.

8. The method of claim 1, wherein the moisture content of the solid material to be biotreated is within the range of 5 to 35% by weight.

* * * * *